US 8,032,014 B2

(12) United States Patent
Cheung

(10) Patent No.: US 8,032,014 B2
(45) Date of Patent: Oct. 4, 2011

(54) FRAGRANCE EMITTING APPARATUS FOR USE WITH USB PORT

(76) Inventor: David Cheung, Hong Kong (CN)

( * ) Notice: Subject to any disclaimer, the term of this patent is extended or adjusted under 35 U.S.C. 154(b) by 344 days.

(21) Appl. No.: 12/295,647

(22) PCT Filed: May 10, 2007

(86) PCT No.: PCT/CN2007/001526
§ 371 (c)(1),
(2), (4) Date: Oct. 1, 2008

(87) PCT Pub. No.: WO2007/137483
PCT Pub. Date: Dec. 6, 2007

(65) Prior Publication Data
US 2009/0261181 A1 Oct. 22, 2009

Related U.S. Application Data

(60) Provisional application No. 60/747,221, filed on May 15, 2006, provisional application No. 60/806,191, filed on Jun. 29, 2006.

(51) Int. Cl.
A61H 33/06 (2006.01)
(52) U.S. Cl. .................................... 392/394; 392/386
(58) Field of Classification Search .......... None
See application file for complete search history.

(56) References Cited

U.S. PATENT DOCUMENTS

| | | | |
|---|---|---|---|
| 4,880,690 A | 11/1989 | Szycher et al. | |
| 6,162,457 A | 12/2000 | Martz | |
| 6,609,935 B2 | 8/2003 | Huang | |
| 7,200,363 B2 | 4/2007 | Greco | |
| 7,203,417 B2 | 4/2007 | Manne | |
| 2003/0206834 A1 | 11/2003 | Chiao | |
| 2004/0235430 A1 | 11/2004 | Ma et al. | |
| 2005/0013728 A1 | 1/2005 | Huang | |
| 2006/0258215 A1 | 11/2006 | Lai et al. | |

FOREIGN PATENT DOCUMENTS

| | | |
|---|---|---|
| CN | 2526001 Y | 12/2002 |
| CN | 2628913 Y | 7/2004 |
| CN | 2672977 Y | 1/2005 |
| CN | 2735677 Y | 10/2005 |
| CN | 1734388 A | 2/2006 |

Primary Examiner — Thor Campbell
(74) Attorney, Agent, or Firm — Raymond A. Nuzzo

(57) ABSTRACT

A fragrance emitting apparatus (20) for connection to a USB port. In one embodiment, the fragrance emitting apparatus (20) comprises a casing (22) having an interior and a fragrance vent (36A, 36B) in communication with the interior, a heating element (42) located within the casing (22) that generates heat when electrical power is applied thereto, a USB connector (28) connected to the casing (22) and electrically connected to the heating element (42) so as to provide electrical power to the heating element (42) when the USB connector (28) is connected to a USB port, and a stationary fragrance member (50) located within the casing (22) to provide a fragrance, scent or aroma when heat is applied to the fragrance member (50). The fragrance member (50) is proximate to the heating element (42) so that heat generated by the heating element (42) causes the fragrance member (50) to emit a fragrance, scent or aroma which exits the interior of the casing (22) through the vent (36A, 36B). Other embodiments of the apparatus of the present invention are disclosed herein.

20 Claims, 28 Drawing Sheets

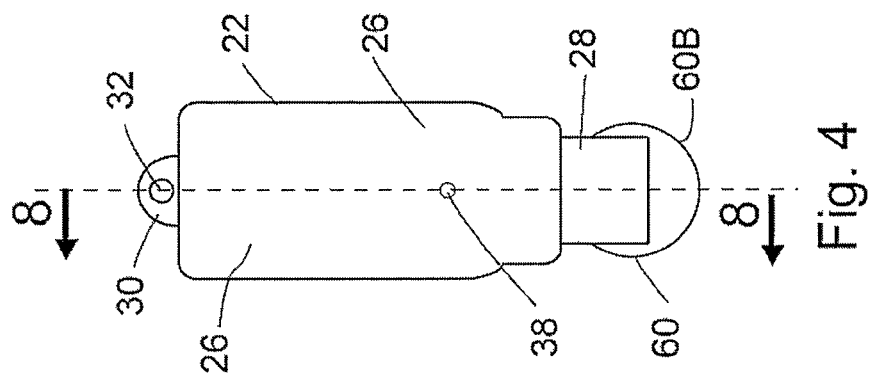
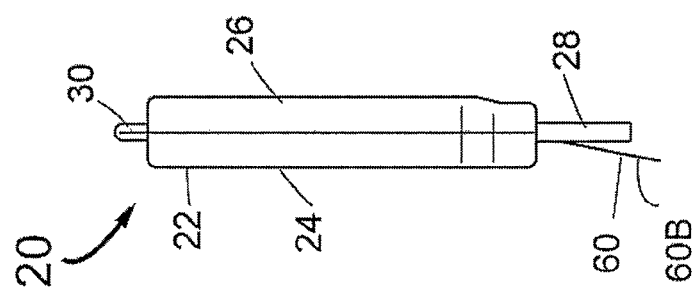
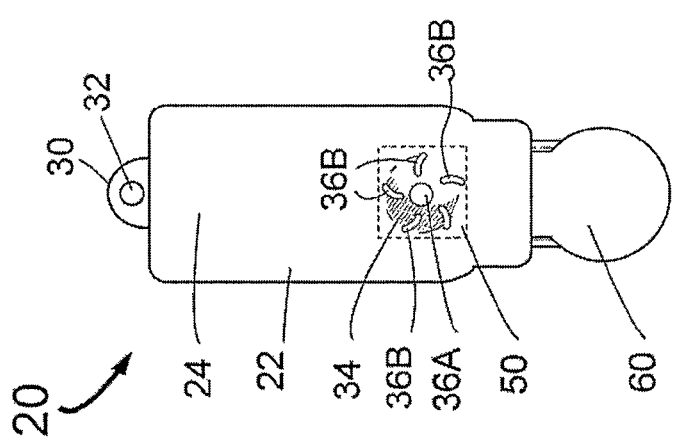
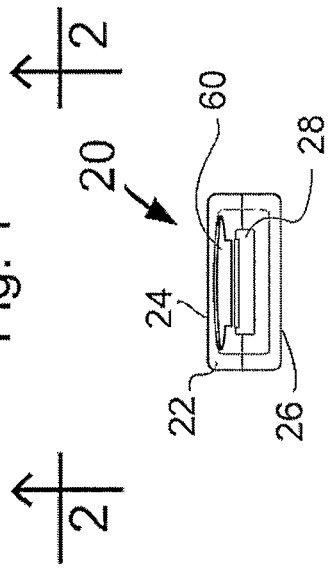

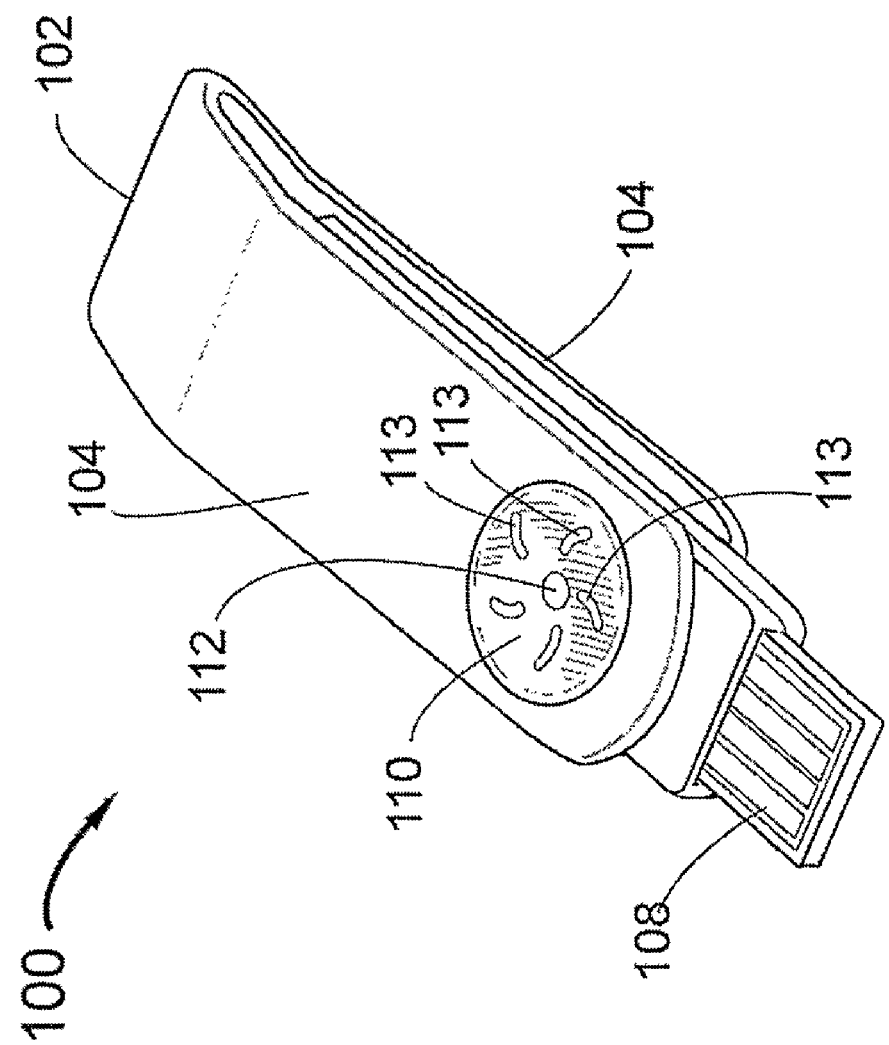

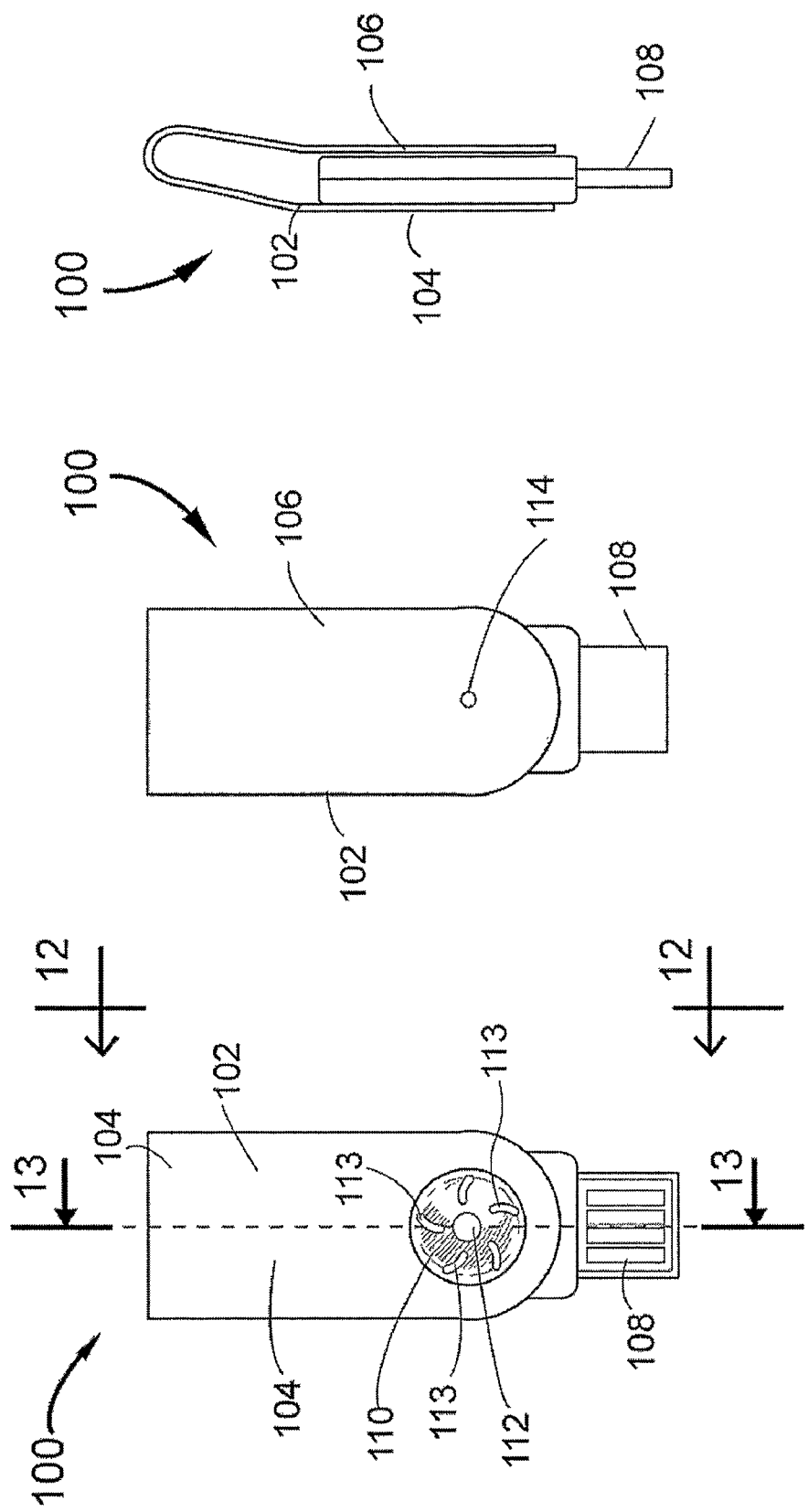

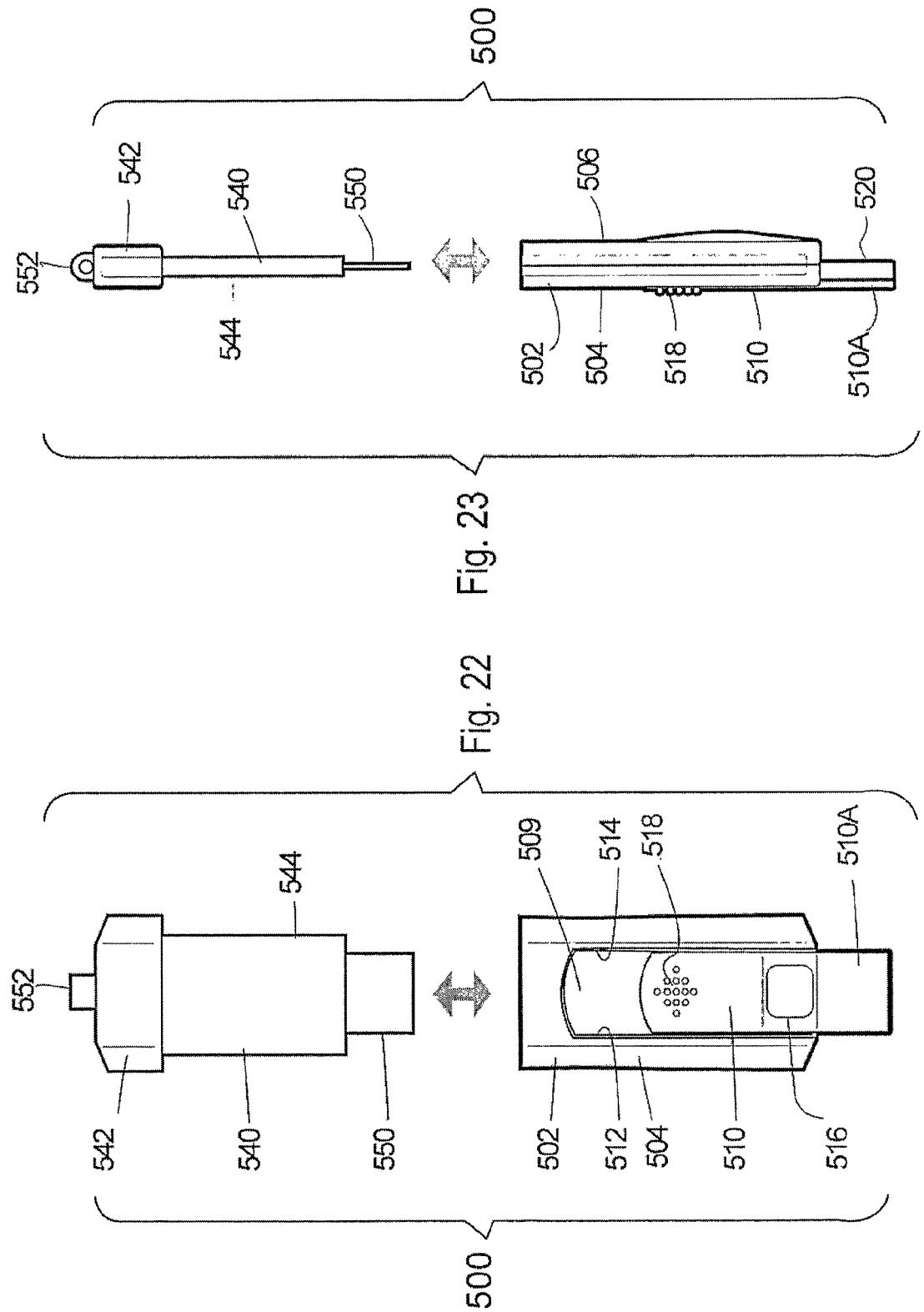

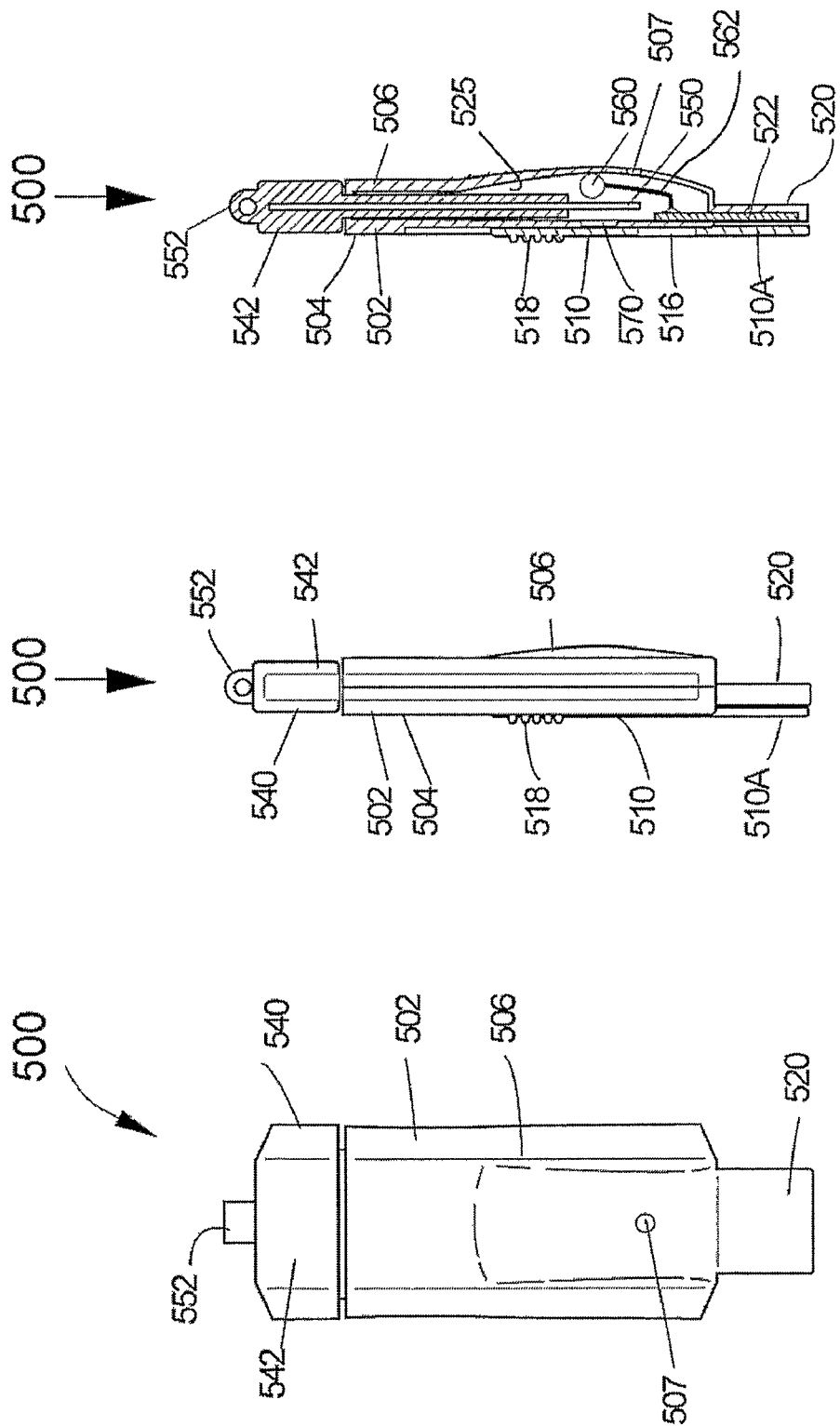

FRAGRANCE EMITTING APPARATUS FOR USE WITH USB PORT

This international patent application claims priority to prior U.S. application No. 60/747,221, filed May 15, 2006, and to prior U.S. application No. 60/806,191, filed Jun. 29, 2006. The entire disclosures of the aforesaid application Nos. 60/747,221 and 60/806,191 are hereby incorporated by reference.

TECHNICAL FIELD

The present invention is generally relates to a fragrance emitting apparatus that is configured to be connected to a USB port of a computer or peripheral device and emit a fragrance when electrical power is provided to a heating element within the fragrance emitting apparatus.

BACKGROUND ART

Electronic devices that are configured to release a fragrance or scent are known in the art. U.S. Patent Application Publication No. US 2003/0206834 entitled "Replaceable Scent And Multimedia Storage For Use With A Playback Apparatus Having Electrostatic Scents Release" describes a scent-bearing and multi-media disk or cartridge for use with separate multi-media playback and scent recovery systems. U.S. Patent Application Publication No. US 2004/0235430 entitled "Mobile Phone And Scent Dispenser Thereof" describes a module phone and a scent dispenser. The scent dispenser includes a body and a scent dispensing device. The body includes a tank and a channel. The tank stores a scent in liquid medium therein. U.S. Patent Application Publication No. US 2005/0013728 entitled "Fragrance Generation Device" describes a fragrance generation device for information products such as a computer, PDA or an electrical appliance. U.S. Pat. No. 7,200,363 entitled "Communication Device Having A Scent Release Feature And Method Thereof" describes a communication device such as a cellular telephone that includes a heat-generating device that generates heat energy. In thermal proximity to the heat-generating device is a scent package that includes a scented substance that is activated by the heat-generating device. U.S. Pat. No. 7,203,417 entitled "Portable Scent Delivery Device" describes a portable scent delivery device that employs a housing and scent generator which selectively releases a scent. The housing is suitably a headset, hat, shoulder harness or personal electronic device like a mobile telephone.

U.S. Pat. No. 6,609,935 (the "'935 patent") discloses a USB Electric Fragrant Emitting Pendant Joint. However, the design of the device shown in the '935 patent is complicated. Specifically, that device uses a rotary fragrance rod that has a ball-shaped end. The ball shaped end is external to the device. The rotary fragrant rod is rotated to a predetermined angle, presumably by the user.

DISCLOSURE OF THE INVENTION

The present invention provides a new and improved fragrance emitting apparatus that can be plugged into a USB port of a computer, a computer peripheral device, or any other device that uses a USB port.

In accordance with one embodiment of the present invention, a fragrance emitting USB pendant device is provided. The fragrance emitting USB pendant device comprises a casing having an interior and a fragrance vent in communication with the interior, a heating element within the casing that generates heat when electrical power is applied thereto, a fragrance member that provides a fragrance, scent or aroma when heat is applied to the fragrance member, and means for positioning the fragrance member proximate to the heating element so that heat generated by the heating element causes the fragrance member to emit a fragrance, scent or aroma that exits the interior of the casing through the fragrance vent. The casing has a top portion and a bottom portion. The fragrance vent is in the top portion. The fragrance vent is aligned with the fragrance member. An air vent is located in the bottom portion of the casing to allow air flow into the interior of the casing. The top portion of the casing has a generally concave-shaped cover portion that is positioned adjacent to the fragrance member. The fragrance vent is generally centrally located in the concave-shaped cover portion. The concave-shape of the concave-shaped cover portion facilitates insertion of a fragrance-emitting substance into the fragrance vent in order to replenish the fragrance member with a fragrance-emitting substance.

In another embodiment, the fragrance emitting apparatus of the present invention comprises a USB flash memory drive that provides a fragrance, scent or aroma when the USB flash memory drive is in use. In one embodiment, the USB flash memory drive comprises a housing having a vent, an electronic component within the housing that generates heat when the USB flash memory drive is in use, a device containing a substance that emits a fragrance, scent or aroma when heat is applied to the device, and means for positioning the device in proximity to the electronic component so that heat generated by the electronic component causes the device to emit the fragrance, scent or aroma. The fragrance, scent or aroma exits the interior of the housing through the vent.

Other embodiments of the present invention are disclosed and described herein.

Other objects and advantages of the present invention will be apparent from the ensuing description and the accompanying drawings.

BRIEF DESCRIPTION OF THE DRAWINGS

The foregoing features of the present invention will become more readily apparent and may be understood by referring to the following detailed description of an illustrative embodiment of the present invention, taken in conjunction with the accompanying drawing, in which:

FIG. 1 is top plan view of the fragrance emitting USB pendant device in accordance with one embodiment of the present invention;

FIG. 2 is an end view taken along line 2-2 in FIG. 1;

FIG. 3 is a side view of the fragrance emitting USB pendant device of FIG. 1;

FIG. 4 is a bottom view of the fragrance emitting USB pendant device of FIG. 1;

FIG. 9 is a perspective view of a fragrance emitting USB pendant device in accordance with another embodiment of the present invention;

FIG. 10 is a top plan view of the fragrance emitting USB pendant device of FIG. 9;

FIG. 11 is a bottom view of the fragrance emitting USB pendant device of FIG. 9;

FIG. 12 is side view taken along line 12-12 of FIG. 10;

FIG. 22 is another exploded, top view of the fragrance emitting apparatus of FIG. 19;

FIG. 23 is a further exploded view of the fragrance emitting apparatus of FIG. 19;

FIG. 24 is a bottom plan view of the fragrance emitting apparatus of FIG. 19;

FIG. 25 is a side view, in elevation, of the fragrance emitting apparatus of FIG. 19, the view showing the air vent cover in the closed position;

FIG. 26 is a cross-sectional view, in elevation, of the fragrance emitting apparatus of FIG. 19, the view showing the air vent cover in the closed position;

BEST MODES FOR CARRYING OUT THE INVENTION

Figure 6:
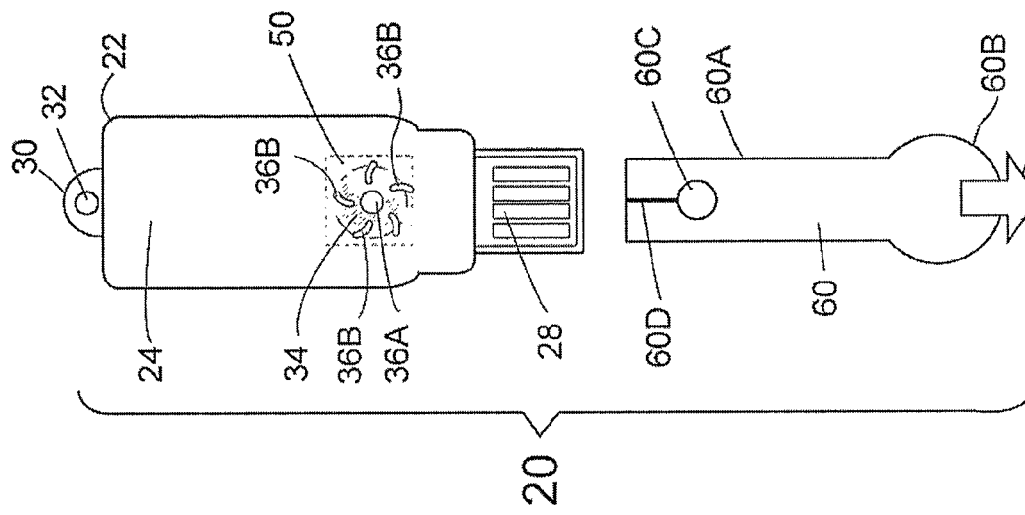
FIG. 6 is an exploded view illustrating the direction in which a protective tab is pulled from the interior of the fragrance emitting USB pendant device of FIG. 1.

Referring to FIGS. 1-4, there is shown fragrance emitting apparatus in accordance with one embodiment of the present invention. In this embodiment, the fragrance emitting apparatus is configured as fragrance emitting USB pendant device 20. For purposes of brevity, fragrance emitting USB pendant device 20 is referred to herein as "USB pendant device 20". USB pendant device 20 generally comprises casing or housing 22 which has top portion 24 and bottom portion 26. USB pendant device 20 further comprises USB connector 28 that is configured to be plugged or inserted into a USB port (not shown) of a computer or a peripheral device.

Referring to FIGS. 1 and 4, casing 22 includes protruding portion 30 that defines opening 32. A key ring chain, string, strap or wire can be inserted into opening 32 so that the USB pendant device 20 can be hung around a user's neck. Top portion 24 of casing 22 includes section 34 which has fragrance vents 36A and 36B from which a fragrance is emitted. Fragrance vent 36A is a central fragrance vent. Air vent 38 is located in bottom portion 26 and allows air to enter the interior of casing 22 (see FIG. 8).

Figure 5:
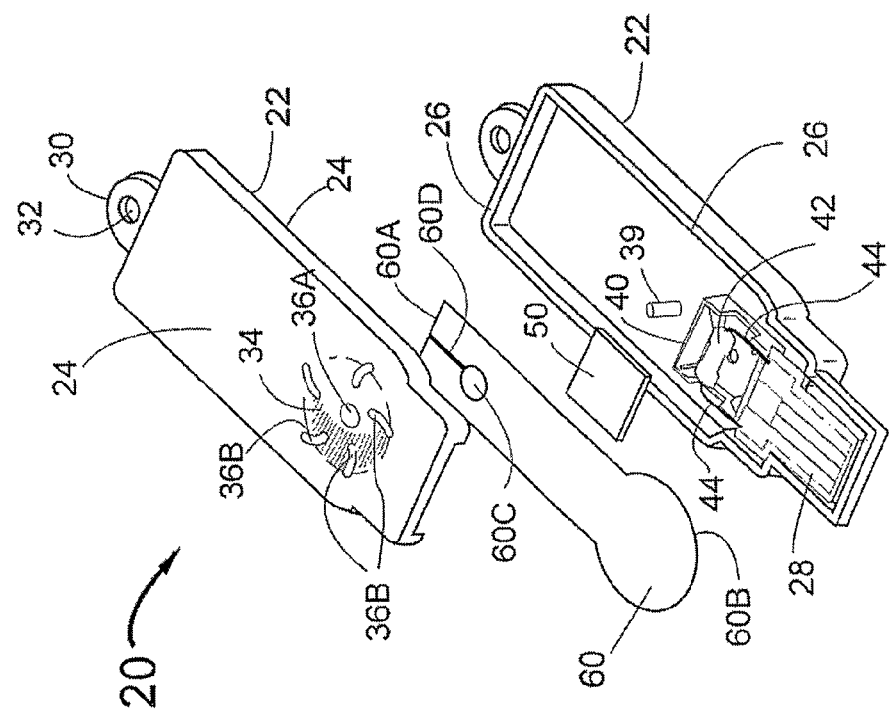
FIG. 5 is an exploded view, in perspective, of the fragrance emitting USB device of FIG. 1.
Figure 7:
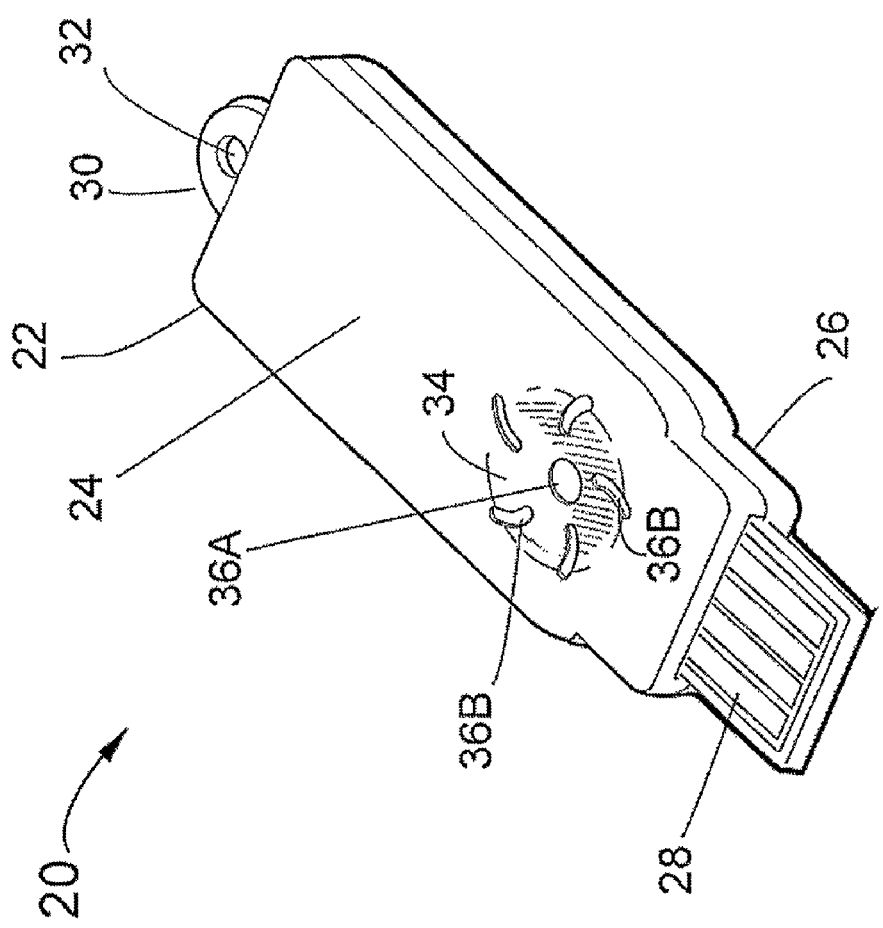
FIG. 7 is a perspective view of the fragrance emitting USB pendant device of FIG. 1 after removal of the protective tab.
Figure 8:
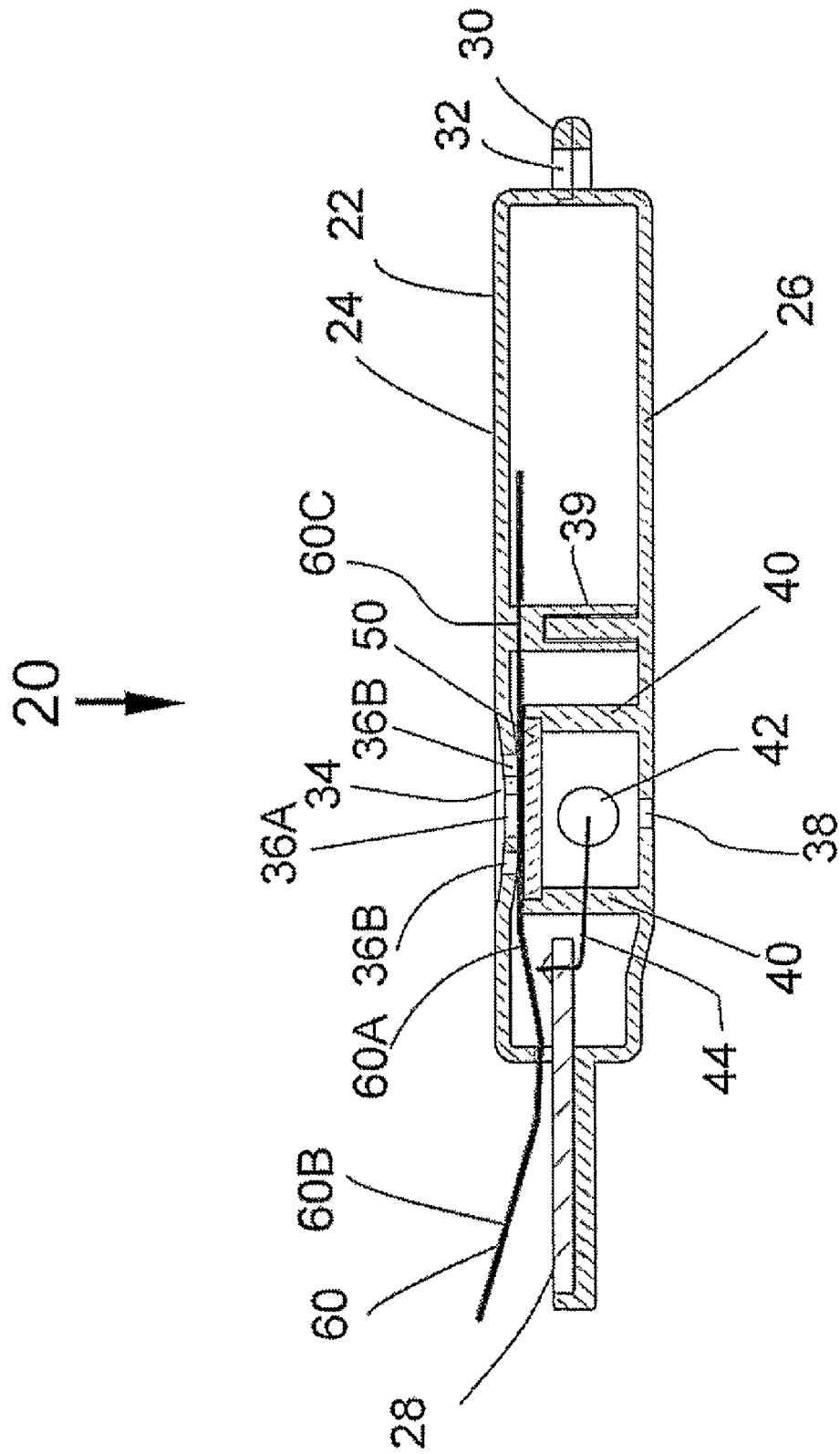
FIG. 8 is a cross-sectional view of the fragrance emitting USB pendant device of FIG. 1.

Referring to FIGS. 5, 6 and 8, USB pendant device 20 includes post 39 and support base 40 that are attached to bottom portion 26 of casing 22. The purpose of post 39 is discussed in the ensuing description. Support base 40 has an interior portion within which is positioned heating element 42. Heating element 42 generates heat when electrical power is applied thereto. Heating element 42 can be almost any type of electrical device that generates heat when electrical power is applied thereto. In this example, heating element 42 is a resistor having electrical conductors 44 that are electrically connected to USB connector 28. When USB connector 28 is connected or inserted into a USB port (not shown) of a computer (not shown) or other peripheral device (not shown), electrical power is provided, via USB connector 28 and electrical conductors 44, to heating element 42.

Referring to FIGS. 5, 6 and 8, USB pendant device 20 further comprises fragrance member 50 that is supported by support base 40 such that fragrance member 50 is positioned over heating element 42. (Fragrance member 50 is shown in phantom in FIG. 1). Fragrance member 50 is entirely located within the interior of casing 22. Thus, no portion of fragrance member 50 is external to casing 22. Fragrance member 50 emits a desired fragrance, scent or aroma when heat is applied thereto. For example, in one embodiment, fragrance member 50 can be configured as an absorbent member that is soaked or saturated with a liquid substance that emits a desired fragrance, scent or aroma when heat is applied thereto. Examples of liquid substances include oils and perfumes. In another embodiment, fragrance member 50 comprises a device that is coated with a substance that emits a desired fragrance, scent or aroma when heat is applied thereto. In another embodiment, fragrance member 50 comprises a capsule or small container that contains a liquid that emits a desired fragrance when heat is applied thereto. Fragrance member 50 can be configured to emit any one of variety of fragrances, aromas or scents, e.g. perfumes, fruit, flowers, etc. In one embodiment, fragrance member 50 has a generally rectangular shape. In another embodiment, fragrance member 50 has a generally square shape, as shown in FIGS. 1 and 5. In a further embodiment, fragrance member 50 has a generally circular, planar shape.

Referring to FIGS. 1 and 3-8, USB pendant device 20 further comprises protective tab 60. Protective tab 60 comprises a first portion 60A that is initially positioned within the interior of USB pendant device 20 and a second portion 60B that is external to casing 22. First portion 60A is positioned between fragrance member 50 and vents 36A and 36B. Protective tab 60 has opening 60C that is adjacent to slit 60D. Opening 60C is sized to receive post 39 (see FIGS. 5 and 8). Protective tab 60 ensures that fragrance member 50 remains fresh and does not experience diminished fragrance emitting efficacy. Thus, protective tab 60 extends the shelf life of fragrance member 50 prior to use. Prior to using USB pendant device 20 for the first time, the user pulls out protective tab 60 in the direction indicated by arrow 70 in FIG. 6. Post 39 slides through slit 60D in protective tab 60. The user can then insert USB connector 28 in a USB port (not shown) of a computer or peripheral device. Once electrical power is applied to USB connector 28, electrical power is applied to heating element 42. In response to the electrical power, heating element 42 generates heat which causes fragrance member 50 to emit a fragrance. The fragrance is emitted through vents 36A and 36B. Air vent 38 allows air to flow into casing 22 to prevent heating element 42 from overheating. In a preferred embodiment, heating element 42 is fixed to the support base 40 so that it is not movable.

Contrary to prior art U.S. Pat. No. 6,609,935 which uses a rotary fragrant rod that is rotated through a predetermined angle, fragrance member 50 of USB pendant device 20 does not rotate. Furthermore, fragrance member 50 is located entirely within the interior of casing 22.

In one embodiment, USB pendant device 20 has an overall shape that is substantially the same as the shape of a USB flash memory drive.

Referring to FIGS. 9-13, there is shown fragrance emitting USB pendant device 100 in accordance with another embodiment of the present invention. USB pendant device 100 generally comprises casing 102. Casing 102 comprises top portion 104 and bottom portion 106. USB pendant device 100 further comprises USB connector 108 which is configured to be plugged into a USB port (not shown) of a computer (not shown) or peripheral device (not shown). Top portion 104 has cover portion 110 which has a concave shape. Cover portion 110 has a plurality of fragrance vents 112 and 113 formed therein, wherein fragrance vent 112 is a central vent and is centrally located in cover portion 110.

Referring to FIGS. 9-13, bottom portion 106 of casing 102 has air vent 114 to allow air to flow into interior 116 of casing 102. Top portion 104 of casing 102 has a support section 120 beneath cover portion 110 so as to define space 122. Support section 120 has a plurality of vents 124 therein. USB pendant device 100 further includes fragrance member 130 that is entirely positioned in space 122. Cover portion 110 is attached to support section 120. Specifically, support section 120 has openings 125 to receive tabs 134 of cover portion 110.

Figure 13:
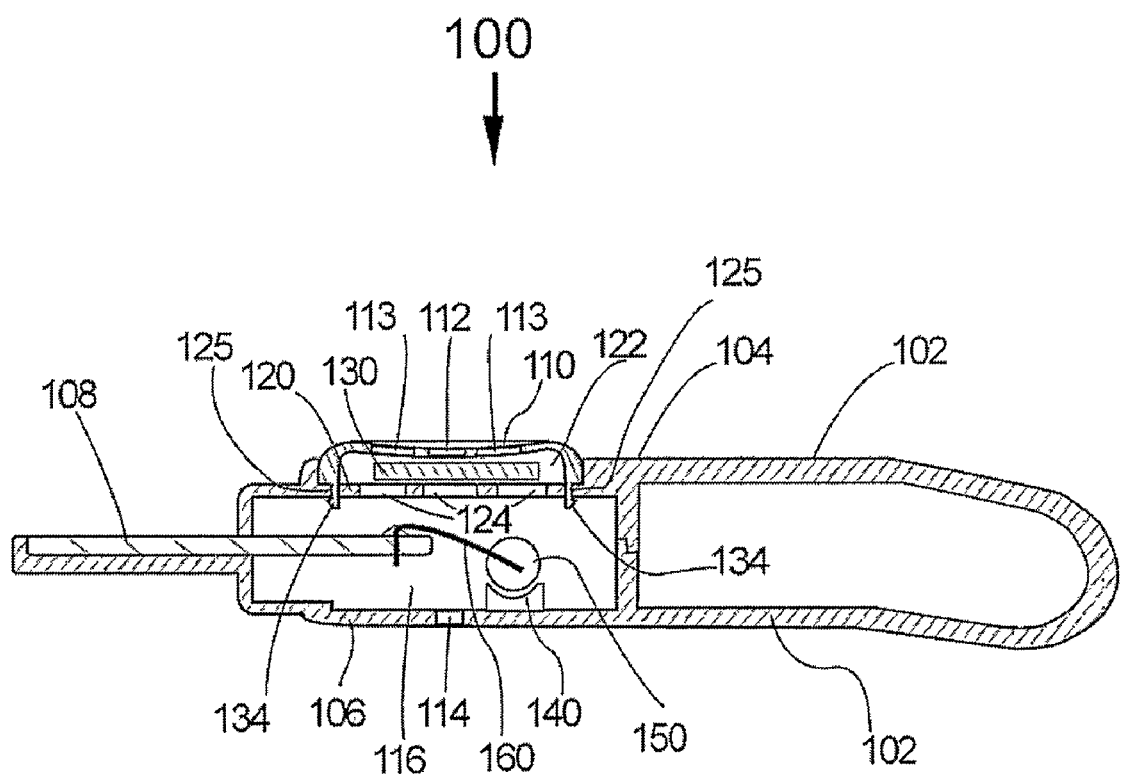
FIG. 13 is a cross-sectional view of the fragrance emitting USB pendant device of FIG. 9.

Referring to FIG. 13, USB pendant device 100 further includes support member 140 that is located within interior 116 and attached to bottom section 106. USB pendant device 100 also includes heating element 150 which is supported by support member 140. Electrical conductor 160 is connected to USB connector 108 and heating element 150. Electrical conductor 160 provides electrical power to heating element 150 when USB connector 108 is plugged into a USB port (not shown). When USB connector 108 is plugged into a USB port of a computer or peripheral device, electrical power is applied to heating element 150 via electrical conductor 160. In response, heating element 150 generates heat which passes through openings 124 in support section 120. This heat causes fragrance member 130 to emit a fragrance. The fragrance is emitted through vents 112 and 113.

A key feature of USB pendant device 100 is that a user may replenish fragrance member 130 with a fragrance producing substance by depositing such substance on the concave-shaped cover portion 110. The concave surface of cover portion 110 enables the fragrance producing substance to flow into central fragrance vent 112 in cover portion 110 and fall or drop onto fragrance member 130. For example, if the fragrance producing substance is an oil or perfume, the user can insert drops of oil into fragrance vent 112. The concave surface of cover portion 110 will cause any excess oil to flow into central fragrance vent 112.

In one embodiment, USB pendant device 100 has an overall shape that is substantially the same as the shape of a USB flash memory drive.

The ensuing description and FIGS. 14-18 are based on prior U.S. application no. 60/747,221, filed May 15, 2006. For purposes of preparing this international application, the reference numbers and drawing figure numbers shown in the aforesaid application no. 60/747,221 have been changed as shown herein in order to avoid confusion. However, it is to be understood that the FIGS. 14-18 and the ensuing description contain the identical subject matter disclosed in the aforesaid U.S. application No. 60/747,221.

Figure 14:
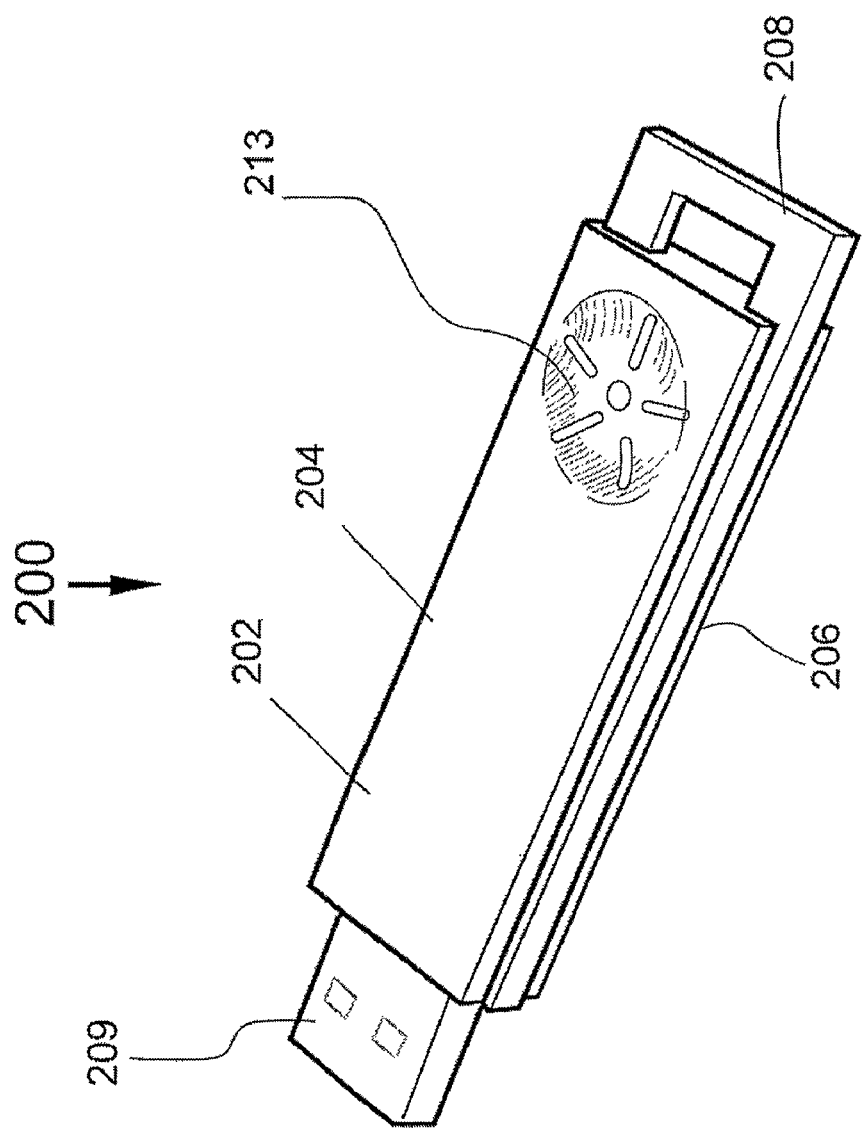
FIG. 14 is perspective view of a fragrance emitting apparatus in accordance with another embodiment of the present invention, the fragrance emitting apparatus being configured as a USB flash memory drive.
Figure 15:
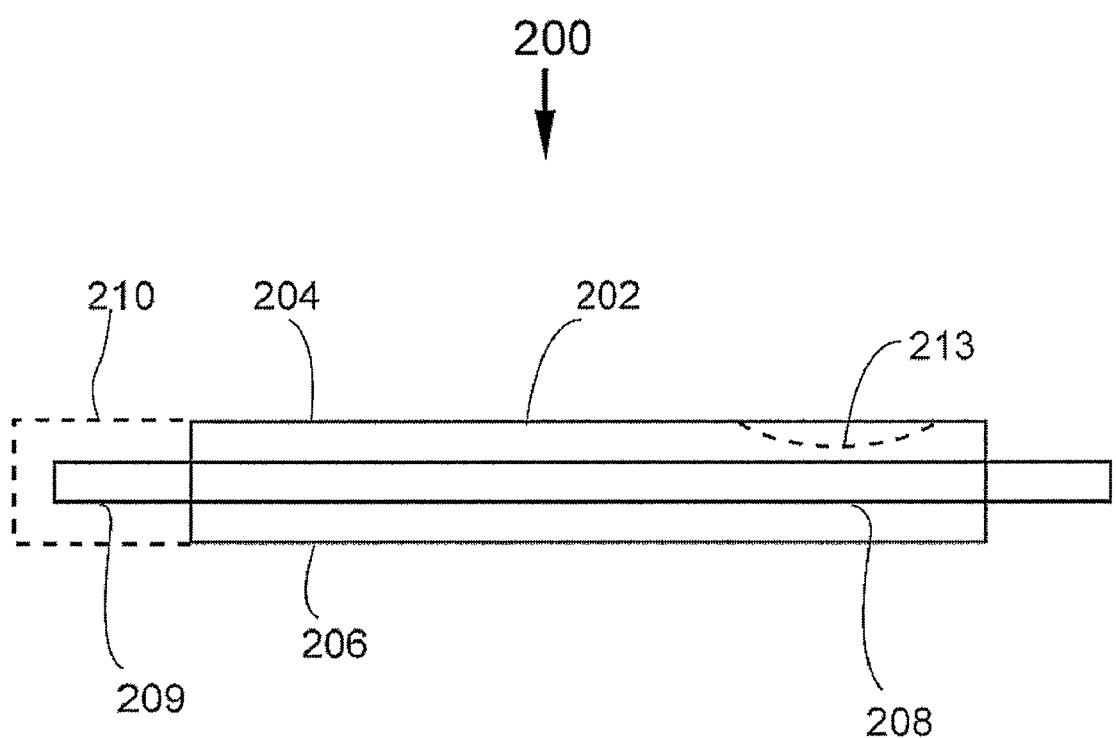
FIG. 15 is a side view of the USB flash memory drive of FIG. 14.

USB (Universal Serial Bus) flash memory drives (also known as USB stick drives) are well known in the computer field and are used to store computer data files. A USB flash memory drive contains a data storage element, such as a memory chip, and other electronic components. When the USB flash memory drive is in use, the data storage element and/or other electronic components generate heat. Thus, in accordance with this embodiment of the present invention, there is shown in FIGS. 14 and 15 a USB flash memory drive 200 which provides a fragrance or aroma when USB flash memory drive 200 is in operation. USB flash memory drive 200 has a housing 202 which comprises top section 204 and bottom section 206. USB flash memory drive 200 further comprises circuit support member 208 that is between top section 204 and bottom section 206. Electrical components, such as memory chips, integrated circuits, or other electronic components, etc. are attached to circuit support member 208. USB connector section 209 is electrically connected to circuit support member 208. USB connector section 209 is configured to be connected or inserted into a USB port of a computer or other data transfer device. Housing 202 further includes cover section 210 (shown in phantom) that covers USB connector section 209. Cover section 210 is removable. Housing 202 includes vent 213 located in the top section 204. The purpose of vent 213 is discussed in the ensuing description.

Figure 16:
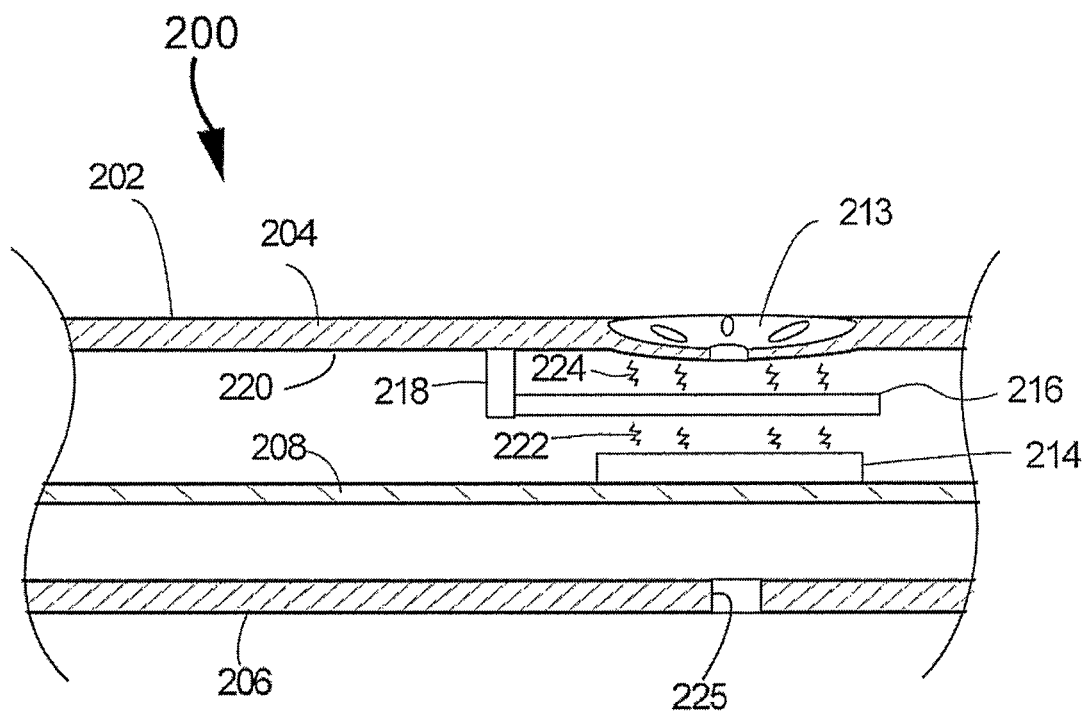
FIG. 16 is a partial, cross-sectional view of the USB flash memory drive of FIG. 14.

Referring to FIG. 16, there is shown a cross-sectional view of USB flash memory drive 200. USB flash memory drive 200 further includes electronic component 214 that is electrically connected to circuit support board 208 and is part of the data storage circuitry and generates heat as a result of the operation of the data storage circuitry. Electronic component 214 can be any electronic component associated with the data storage circuitry, e.g. integrated circuit, resistor, etc. In an alternate embodiment of the invention, electronic component 214 is added specifically to circuit support board 208 for the purpose of generating heat and is not pertinent to the data storage function of USB flash memory drive 200. In accordance with the invention, USB flash memory drive 200 further comprises device 216 that emits a fragrance, scent or aroma when heat is applied thereto. Device 216 can have any one of several configurations. For example, device 216 can be configured to contain or hold a liquid or solid substance that emits a desired fragrance, scent or aroma when heat is applied thereto. Examples of a liquid substance include oils and perfumes. In another example, device 216 is coated with a substance that emits a desired fragrance, scent or aroma when heat is applied thereto. In a further example, device 216 comprises an absorbent member that is soaked or saturated with a liquid substance that emits a desired fragrance, scent or aroma when heat is applied thereto. Other configurations for device 216 are possible. Device 216 can be configured to emit any one of variety of fragrances, aromas or scents, e.g. perfumes, fruit, flowers, etc. Device 216 is attached to support member 218. In one embodiment, support member 218 is attached to interior wall 220 of housing 202 and is adjacent to vent 213. Support member 218 is shaped and configured so as to allow device 216 to be positioned over and very close to electronic component 214. When USB flash drive 200 is plugged into a USB port, electrical power is applied to electronic component 214 which, in response, generates heat 222. Heat 222 causes device 216 to emit a fragrance, scent or aroma 224 that passes through vent 213. In a preferred embodiment, housing 202 further includes vent 225. Vent 225 is located in bottom section 206 of housing 202. Vent 225 allows airflow into the interior of housing 202 to prevent overheating of the electronic components therein.

Figure 18:
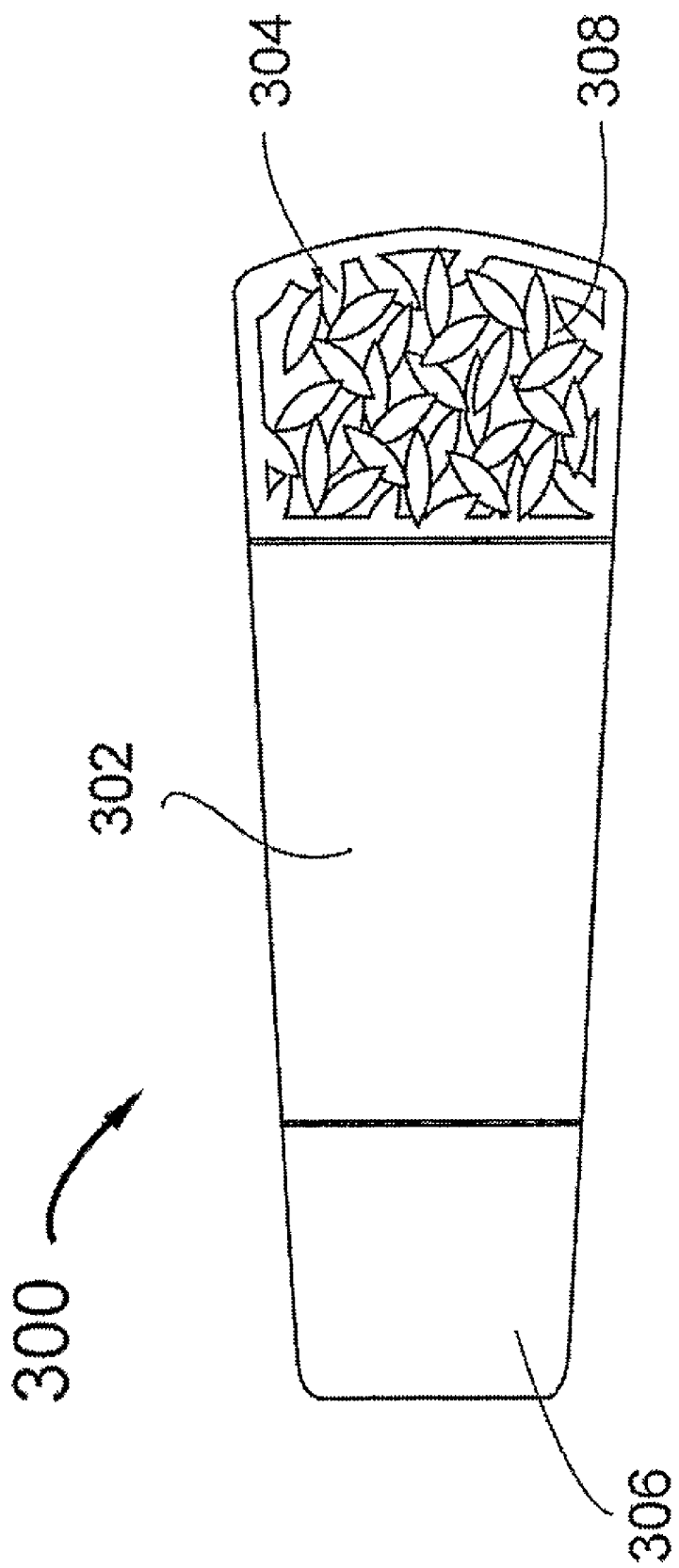
FIG. 18 is a top view of a further embodiment of the USB flash memory drive.
Figure 19:
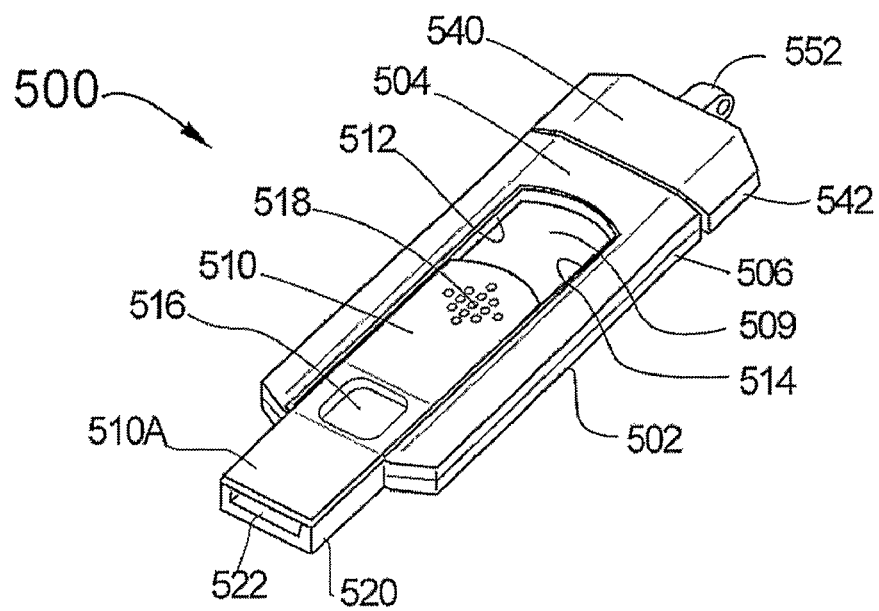
FIG. 19 is a perspective view of a fragrance emitting apparatus in accordance with another embodiment of the present invention, the view showing an air vent cover of the fragrance emitting apparatus being in a closed position.
Figure 20:
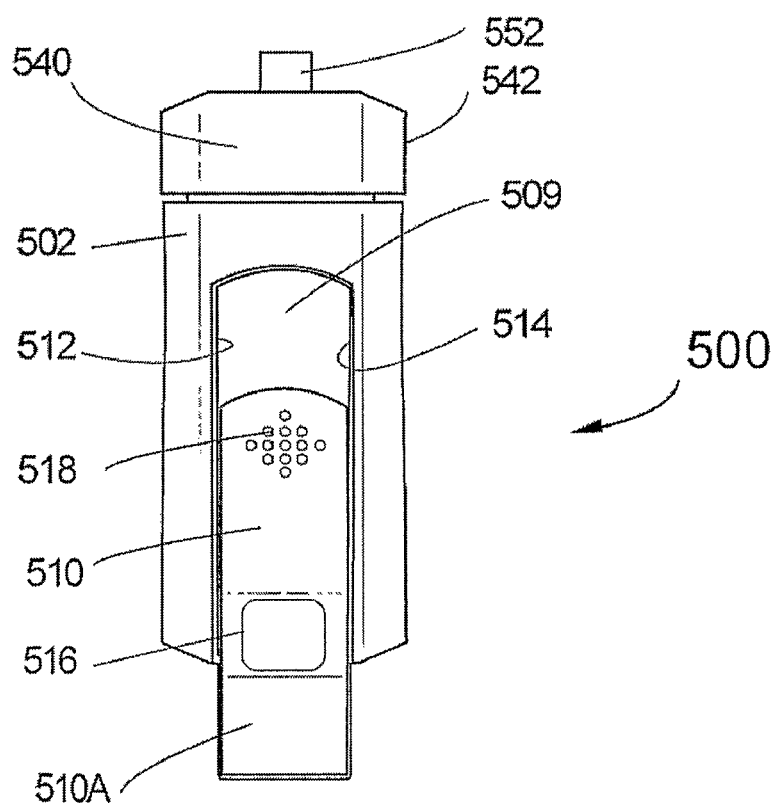
FIG. 20 is a top plan view of the fragrance emitting apparatus of FIG. 19.

Housing 202 can be configured to have any one of a variety of suitable shapes and designs. One example is shown in FIG. 14. Another example is shown in FIG. 18. USB flash memory drive 300 comprises housing 302 which has a rounded end portion 304 and a tapered geometry. Housing 302 includes cover section 306 that covers the USB connector section (not shown but generally the same as USB connector section 209 shown in FIG. 15). Housing 302 includes a stylish vent section 308 from which the fragrance, scent or aroma exits the interior of the housing.

Figure 17:
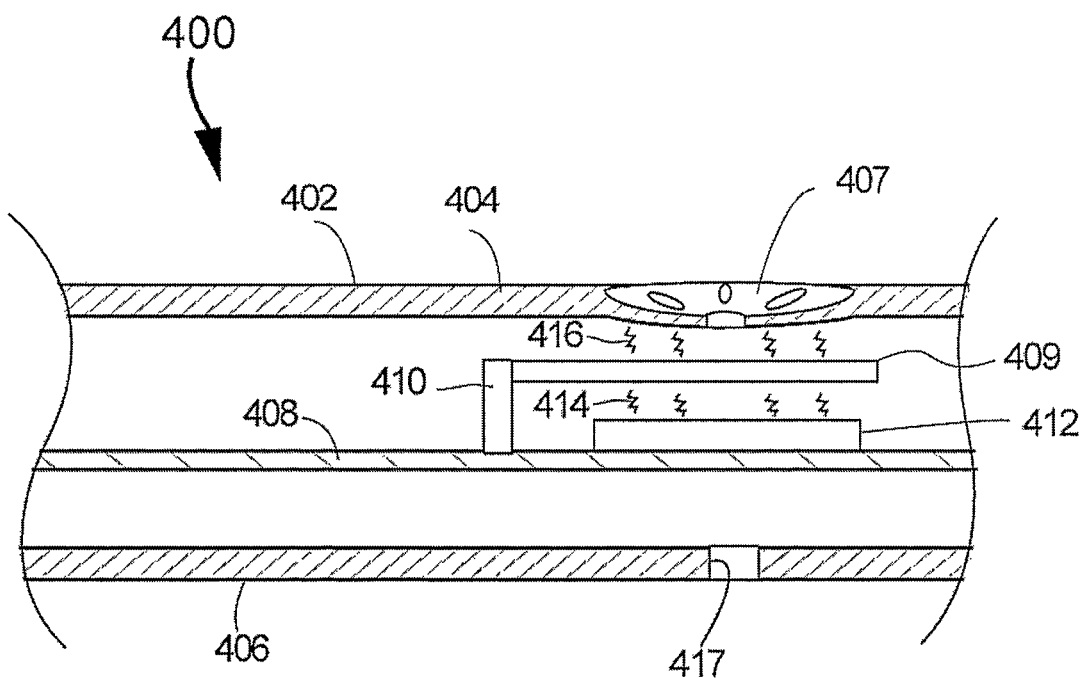
FIG. 17 is a partial, cross-sectional view of an alternate embodiment of the USB flash memory drive.

FIG. 17 shows a partial, cross-sectional view of USB flash memory drive 400 in accordance with an alternate embodiment of the invention. USB flash drive 400 comprises housing 402 which has top portion 404 and bottom portion 406. Housing 402 includes vent 407 in top portion 404. Vent 407 is similar to vent 213 (see FIGS. 14 and 15). USB flash memory drive 400 further includes circuit support member 408 and device 409 which emits a fragrance, scent or aroma when heat is applied thereto. In accordance with this embodiment, device 409 is connected to support member 410 which is connected to circuit support member 408. USB flash memory drive 400 further comprises an electronic component 412 that is electrically connected to circuit support member 408 and which generates heat 414 in a manner similar to electronic component 214 (see FIG. 16). Thus, electronic component 412 generates heat 414 when electrical power is applied to electrical component 412. Support member 410 is shaped and configured to position device 409 over and close to heat generating electronic component 412. The heat 414 generated by electronic component 412 causes a fragrance, scent or aroma 416 to be emitted by device 409. The fragrance, scent or aroma 416 exits the interior of the housing 402 by vent 407. In a preferred embodiment, housing 402 further includes vent 417. Vent 417 is located in bottom portion 406 of housing 402. Vent 417 allows airflow into the interior of housing 402 to prevent overheating of the electronic components therein.

Referring to FIGS. 19-30, there is shown fragrance emitting apparatus 500 in accordance with another embodiment of the present invention. In this embodiment, fragrance emitting apparatus 500 has an appearance similar to that of a flash memory drive. Apparatus 500 generally comprises casing 502 that has top section 504 and bottom section 506. Bottom section 506 has a vent 507 (see FIG. 24) that allows air to flow into interior 525 of casing 502. Top section 502 has a recessed area 509. Apparatus 500 further includes air vent cover 510. Air vent cover 510 includes portion 510A. Air vent cover 510 is slidably attached to casing 502. Specifically, air vent cover 510 can bi-directionally slide within recessed area 509. Top section 502 includes tracks 512 and 514 that are in either side of recessed area 509. Air vent cover 510 is slidably engaged to tracks 512 and 514. Air vent cover 510 has a vent 516. The purpose of vent 516 is discussed in the ensuing description. Vent cover 510 has a plurality of projections 518 that provide a frictional surface for a user's finger. Thus, projections 518 facilitate sliding air vent cover 510 bi-directionally to either a closed or open position. Apparatus 500 further includes USB connector 520 that is configured to be plugged into a USB port (not shown) of a computer or of a computer peripheral device, or any other electronic device that employs a USB port (see FIGS. 21 and 23). USB connector 520 has a printed circuit section 522 (see FIGS. 27 and 28). The portion 510A of the vent cover 510 covers USB connector 520 when air vent cover 510 is in the closed position.

Figure 21:
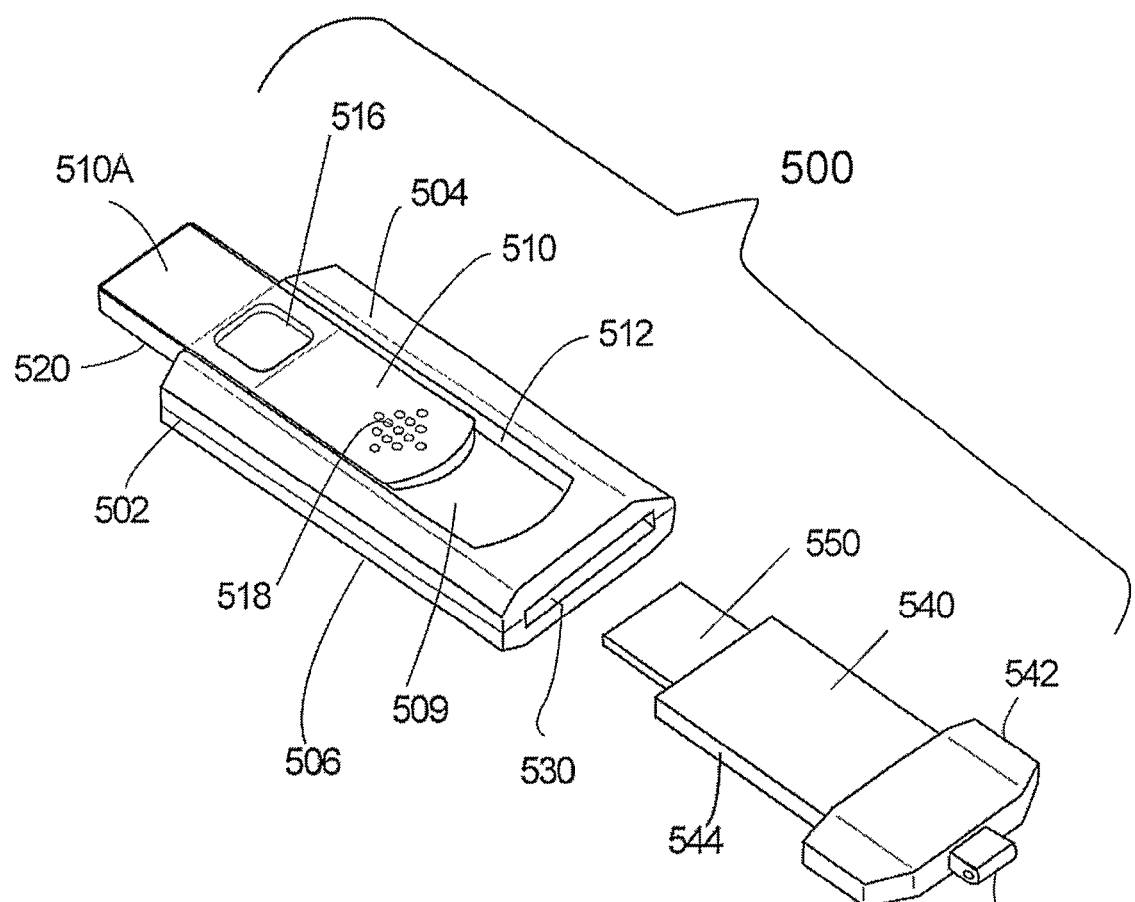
FIG. 21 is an exploded view, in perspective, of the fragrance emitting apparatus of FIG. 19.
Figure 27:
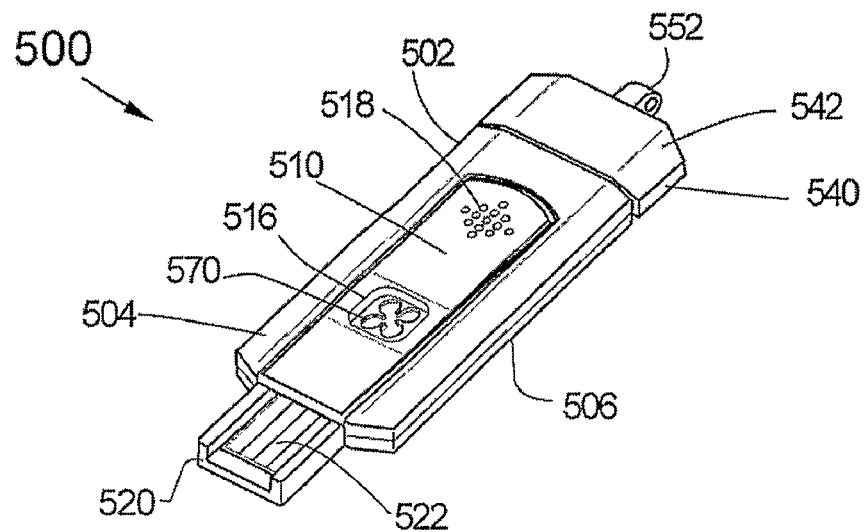
FIG. 27 is a perspective view of the fragrance emitting apparatus of FIG. 19, the view showing the air vent cover in an open position.
Figure 28:
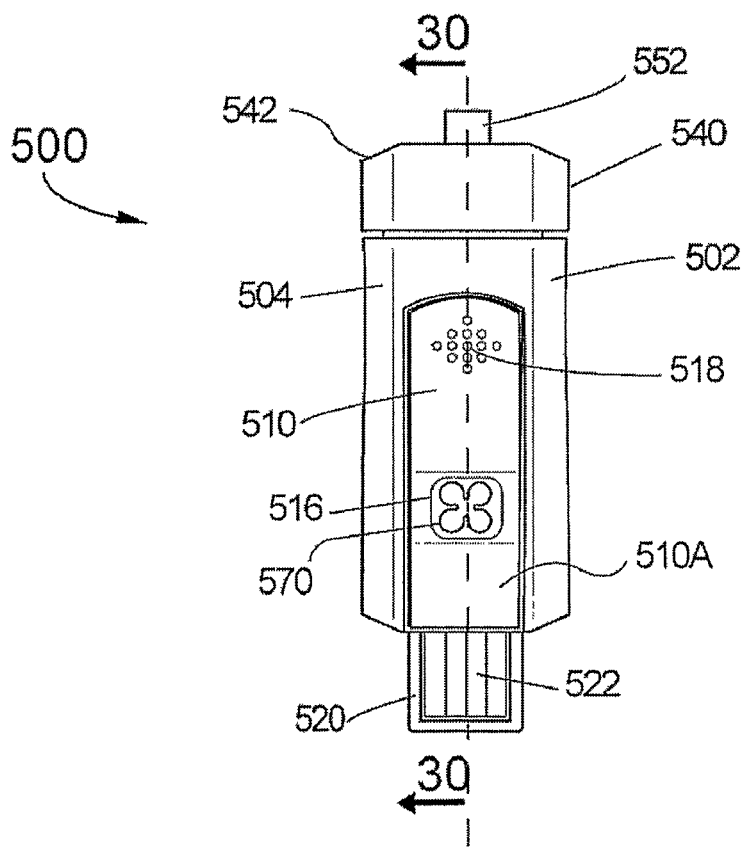
FIG. 28 is a top plan view of the fragrance emitting apparatus as shown in FIG. 27, the view showing the air vent cover in an open position.
Figure 29:
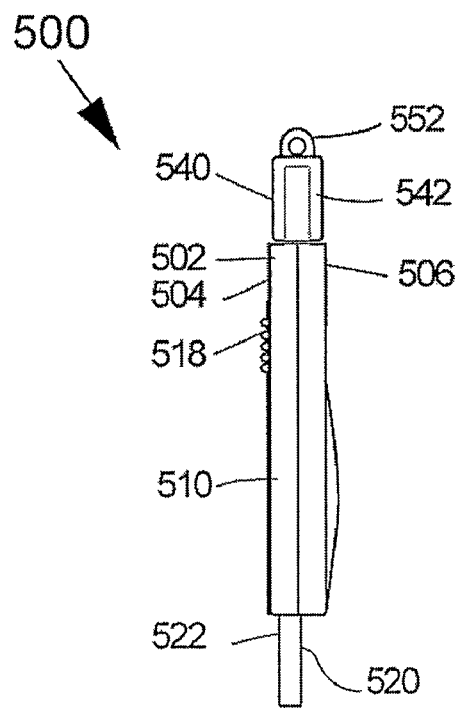
FIG. 29 is a side view, in elevation, of the fragrance emitting apparatus as shown in FIG. 28, the view showing the air vent cover in an open position.
Figure 30:
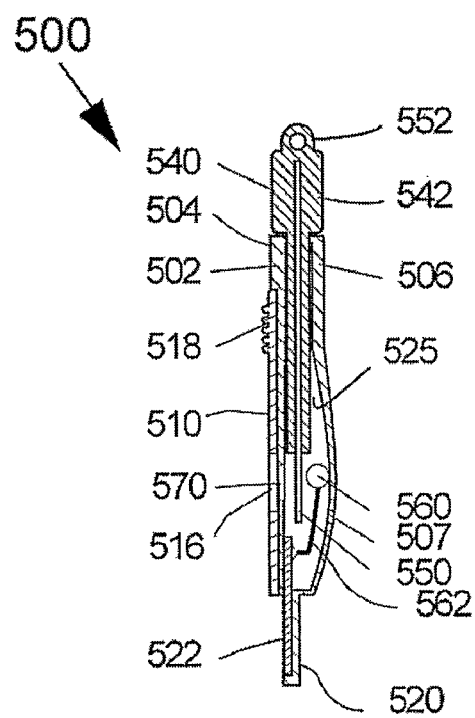
FIG. 30 is a cross-sectional view taken along line 30-30 in FIG. 28.

Referring to FIG. 21, casing 502 has an interior 525 and an opening 530 in communication with interior 525. Apparatus 500 further comprises cartridge case 540 that has section 542 and section 544. Fragrance member 550 is attached to section 544. Fragrance member 550 emits a desired fragrance, scent or aroma when heat is applied thereto. For example, in one embodiment, fragrance member 550 can be configured as an absorbent member that is soaked or saturated with a liquid substance that emits a desired fragrance, scent or aroma when heat is applied thereto. Examples of liquid substances include oils and perfumes. In another embodiment, fragrance member 550 comprises a device that is coated with a substance that emits a desired fragrance, scent or aroma when heat is applied thereto. Fragrance member 550 can be configured to emit any one of variety of fragrances, aromas or scents, e.g. perfumes, fruit, flowers, etc. In one embodiment, fragrance member 550 has a generally square shape. However, fragrance member 550 can be configured to have other shapes as well. Section 542 of casing 540 includes eyelet 552 that is sized to receive a strap or chain which the user can place around his or her neck. Opening 530 is sized to receive section 544 of cartridge case 540. Interior 525 of casing 502 is sized to receive fragrance member 550 and all of section 544 of cartridge case 540. Thus, cartridge case 540 can be removably secured to casing 502 by inserting section 544 into opening 530 and sliding section 544, and fragrance member 550 into interior 525. Casing 502 is structured so that there is a slight frictional relationship between the inner structure of casing 502 and section 544 of cartridge case 540 so that cartridge case 540 does not slip out from interior 525. A user can remove cartridge case 540 and replace it with another cartridge case 540 having a fresh fragrance member 550.

Referring to FIGS. 25 and 26, fragrance emitting apparatus 500 further comprises heating element 560 located in interior 525. Heating element 560 can be realized by any one of a variety of electrical components that generate heat when electrical power is applied thereto. In one embodiment, heating element 560 is a resistor having electrically conductive leads or wires 562 that are electrically connected to printed circuit section 522 of USB connector 520. Electrically conductive leads 562 have a degree of stiffness to keep resistor 560 in proximity to fragrance member 550. When USB connector 520 is plugged into a USB port (not shown) of a computer or computer peripheral device, electrical power is provided to printed circuit section 522. As a result, electrical power is applied to resistor 560 that causes resistor 560 to generate heat. Top section 504 of casing 502 has vent 570 that is in proximity to and aligned with fragrance member 550. When air vent cover 510 is slid to the closed position, as shown FIGS. 19, 20, 25 and 26, the portion 510A of air vent cover 510 completely covers printed circuit section 522 and the other portion of air vent cover 510 covers vent 570. When air vent cover 510 is slid to the open position, as shown in FIGS. 27-30, vent 516 in air vent cover 510 is positioned over and is aligned with air vent 570. Thus, when fragrance member 550 is plugged into a USB port of a computer or a peripheral device and air vent cover 510 is slid into the open position, electrical power is applied to resistor 560 thereby causing resistor 560 to generate heat. This heat causes fragrance member 550 to emit a fragrance which passes through vents 570 and 516 and into the surrounding environment.

Figure 35:
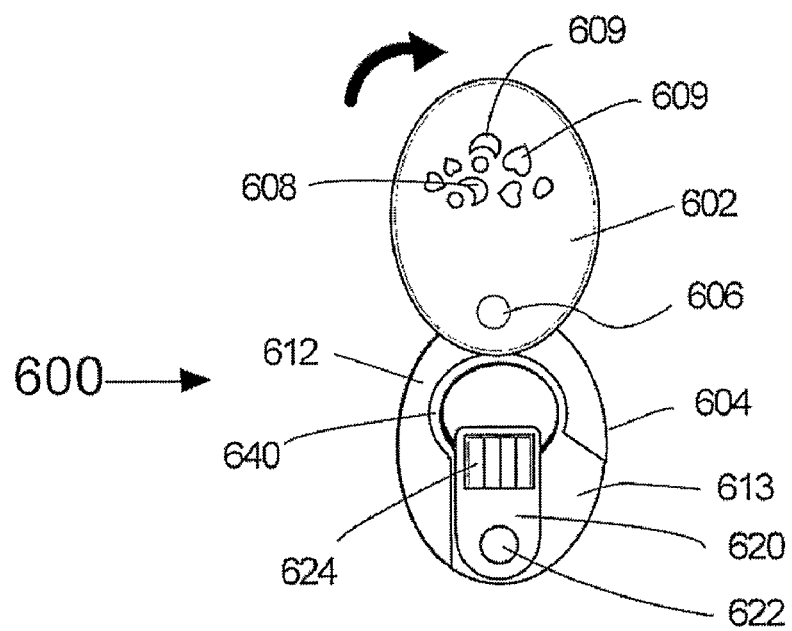
FIG. 35 is a top view of the fragrance emitting apparatus of FIG. 31, the view showing the cover pivoted to an open position.
Figure 36:
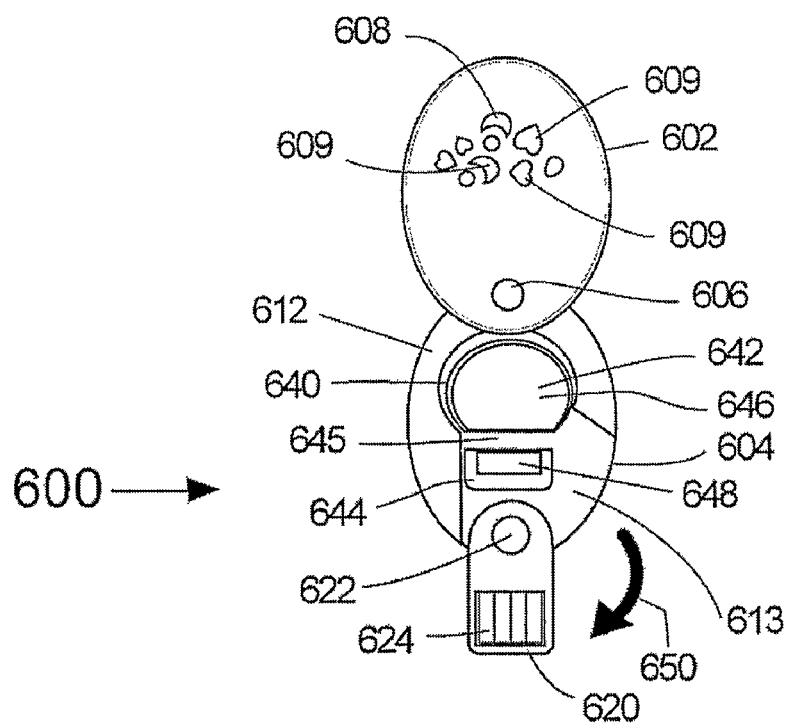
FIG. 36 is a top view of the fragrance emitting apparatus of FIG. 31, the view showing the cover pivoted to an open position and a USB connector pivoted to an exposed position.
Figure 37A:
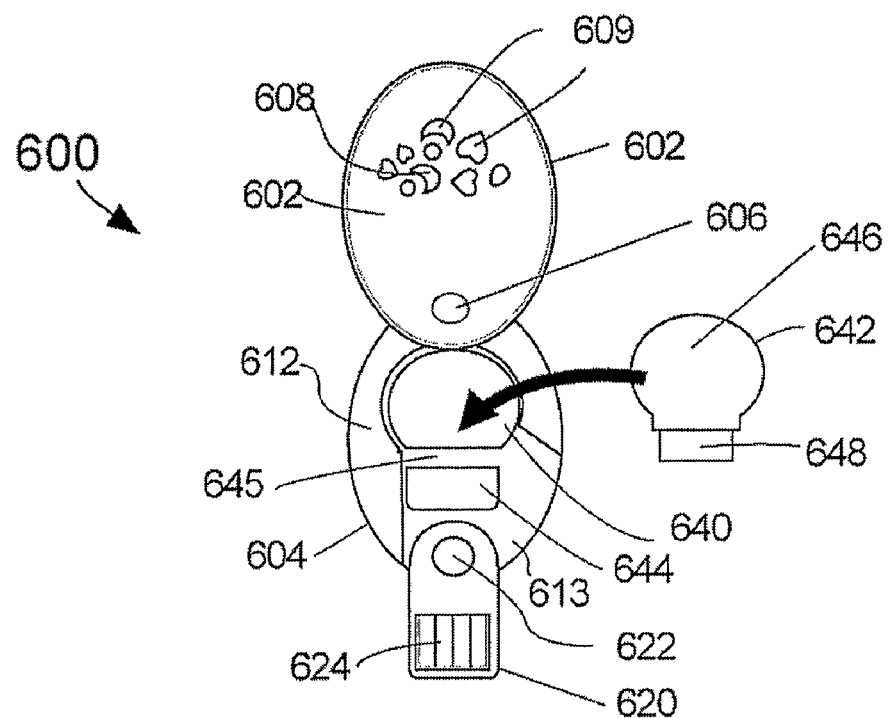
FIG. 37A is a front view of the fragrance emitting apparatus of FIG. 31 and a removable cartridge that is removably positioned within the casing of the fragrance emitting apparatus.
Figure 37B:
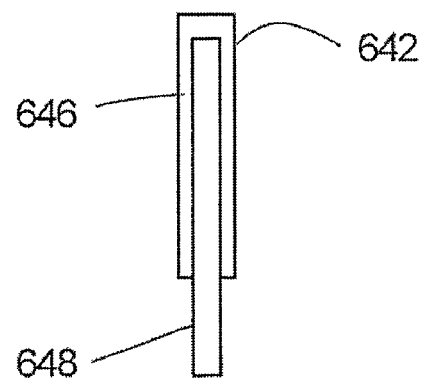
FIG. 37B is side view, in elevation, of the cartridge shown in FIG. 37A.
Figure 38:
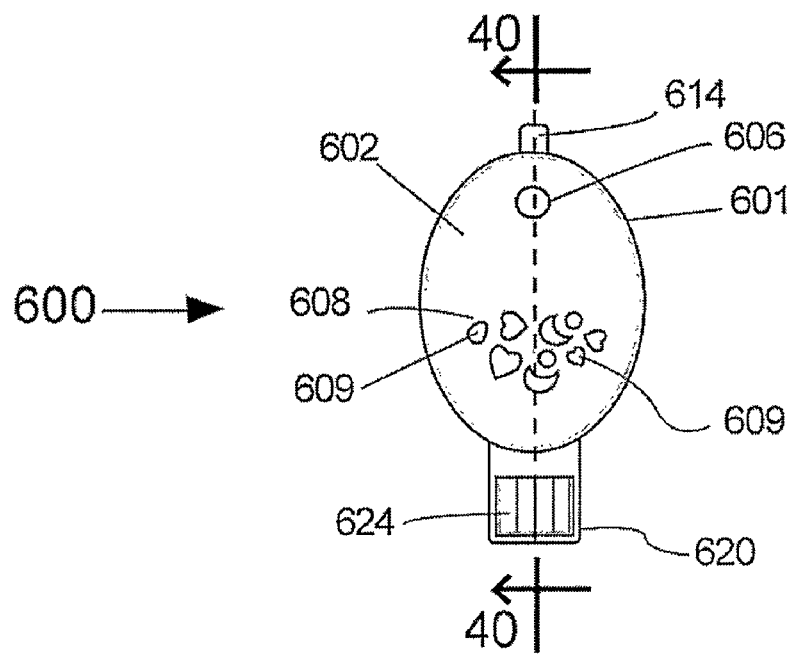
FIG. 38 is a top view of the fragrance emitting apparatus of FIG. 31, the view showing the cover in a closed position and the USB connector pivoted to an exposed position.
Figure 39:
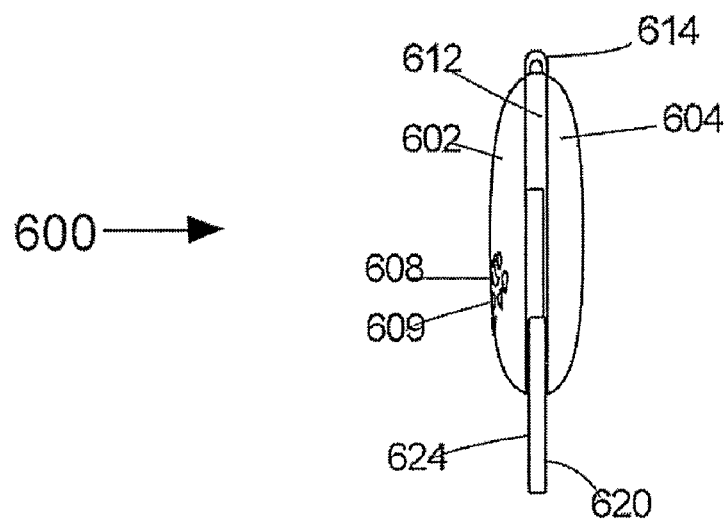
FIG. 39 is side view, in elevation, of the fragrance emitting apparatus, as shown in FIG. 38.
Figure 40:
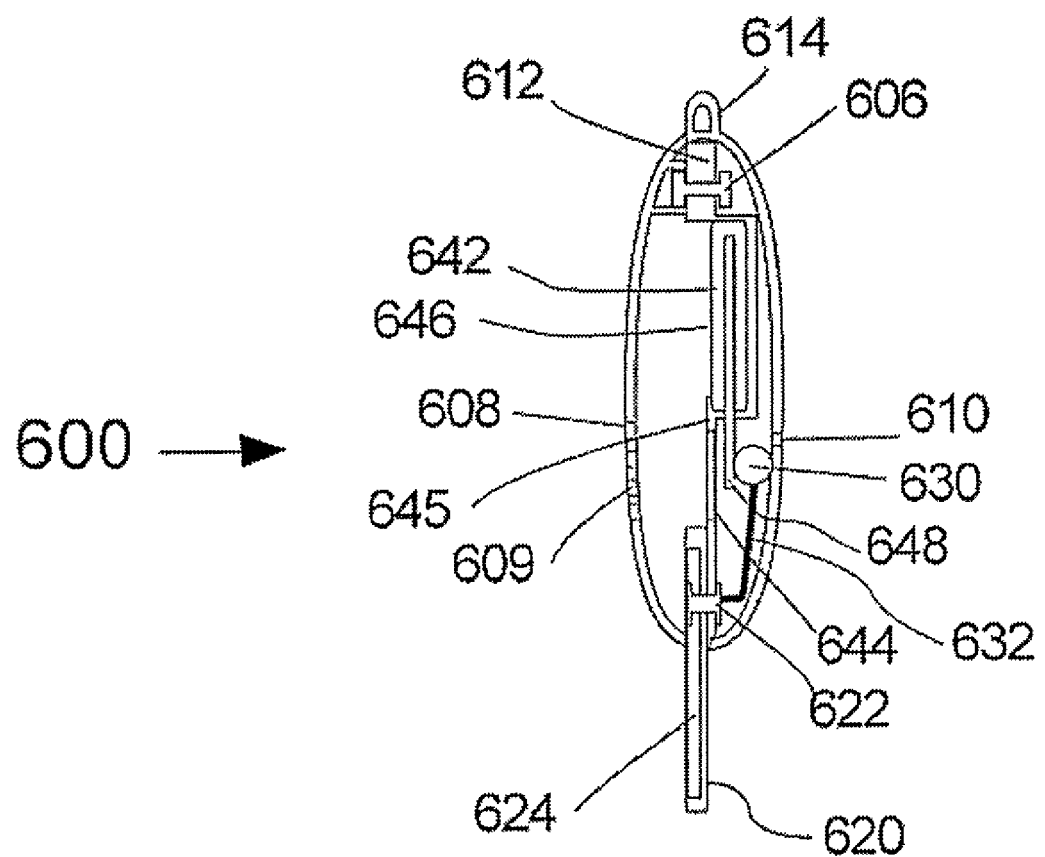
FIG. 40 is a cross-sectional view taken along line 40-40 of FIG. 38.

Referring to FIGS. 31-40, there is shown fragrance emitting apparatus 600 in accordance with a further embodiment of the present invention. In this particular embodiment, apparatus 600 has the shape of a piece of jewelry. However, it is to be understood that apparatus 600 can be configured to have other shapes as well. Apparatus 600 comprises casing 601 having top section 602 and bottom section 604. Top section 602 is rotatably attached to bottom section 604 at rotation joint 606 (see FIGS. 31 and 35). Top section 602 has air vent 608 therein that comprises a plurality of differently shaped openings 609. Bottom section 604 has an air vent 610 (see FIG. 33). Bottom section 604 also includes top portion 612 (see FIGS. 35, 36 and 38). Top portion 612 has recess 613, the purpose of which will be discussed in the ensuing description. Apparatus 600 further includes a strap or chain loop 614 that is attached to bottom section 604 and which is configured to receive chain or strap 616. A user can place chain or strap 616 around his or her neck. In a preferred embodiment, top section 602 can rotate 360° with respect to bottom section 604 as shown in FIGS. 35, 36 and 37A.

Figure 31:
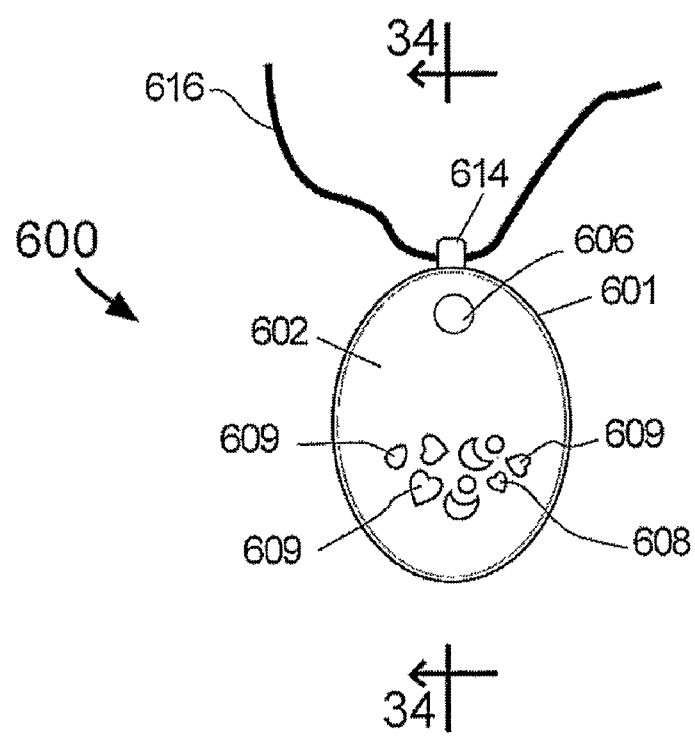
FIG. 31 is a top view of a fragrance emitting apparatus in accordance with a further embodiment of the present invention.
Figure 32:
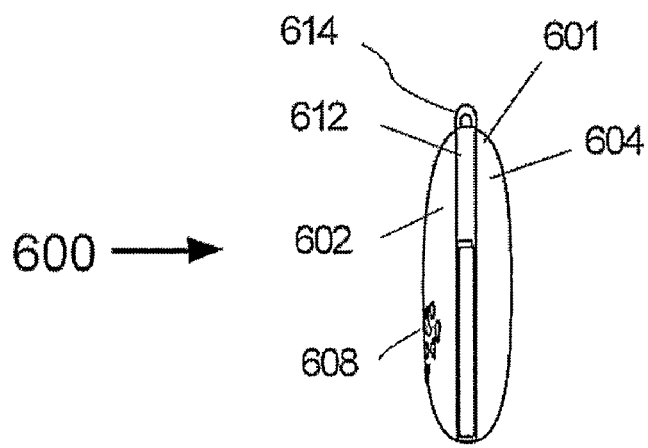
FIG. 32 is a side view, in elevation, of the fragrance emitting apparatus of FIG. 31.
Figure 33:
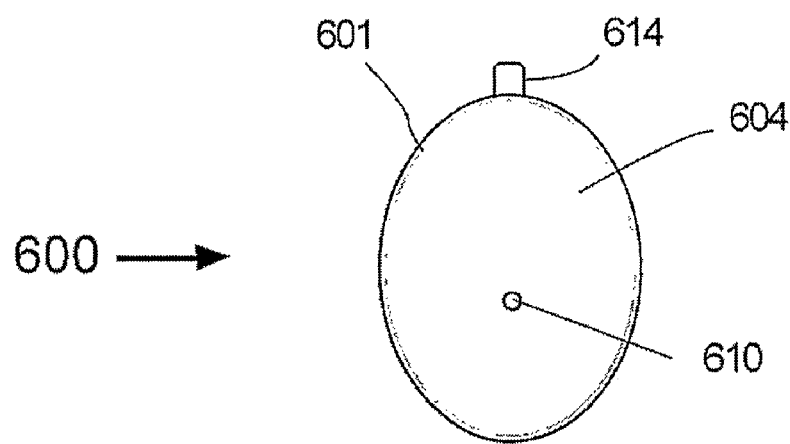
FIG. 33 is a bottom view of the fragrance emitting apparatus of FIG. 31.
Figure 34:
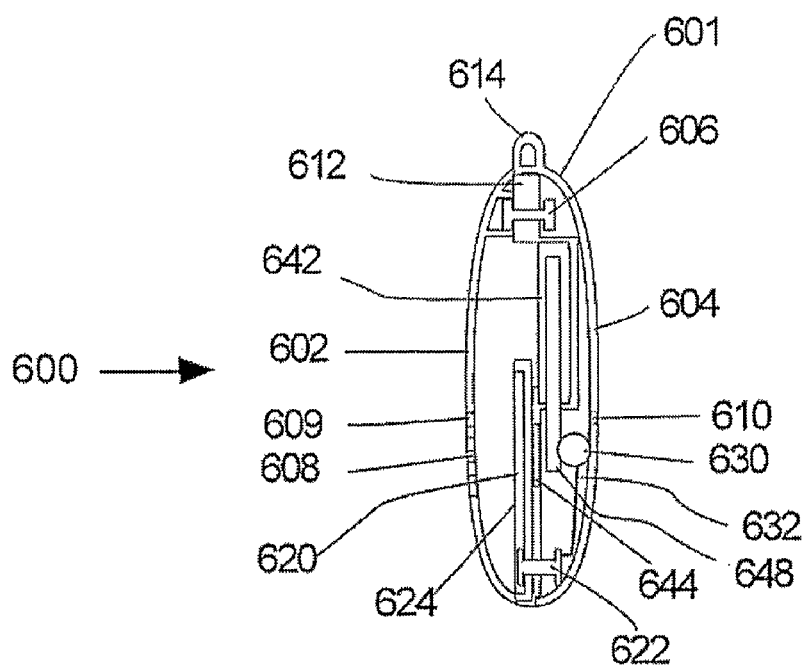
FIG. 34 is a cross-sectional view taken along line 34-34 of FIG. 31.

Referring to FIGS. 34-37A, apparatus 600 further comprises USB connector 620 that is pivotally attached to bottom section 604 at joint or pin 622. USB connector 620 is configured to be plugged into a USB port (not shown) of a computer or a peripheral device. USB connector 620 has printed circuit section 624. USB connector 620 pivots within recess 613 and allows the user to pivot USB connector 620 upward as shown in FIG. 35 or downward as shown in FIG. 36. Once USB connector 620 is pivoted upward as shown in FIG. 35, the user can then pivot top section 602 downward as shown in FIGS. 31 and 32 so as to cover USB connector 620. Joint or pin 622 is electrically conductive and is electrically connected to printed circuit section 624 of USB connector 620. Apparatus 600 further comprises heating element 630 which generates heat when electrical power is applied thereto. Heating element 630 can be any device or electrical component that generates heat when electrical power is applied thereto. In one embodiment, heating element 630 is a resistor. Heating element 630 is electrically connected to joint or pin 622 via electrically conductive lead or leads 632. When USB connector 620 is plugged into a USB port, electrical power is applied to printed circuit section 624, pin or joint 622, lead 632, and thus heating element 630. As a result, heating element 630 generates heat. This feature is further discussed in the ensuing description.

Referring to FIGS. 36, 37A, 37B and 40, bottom section 604 has an opening 640 that is sized to receive cartridge 642. Bottom section 604 also has opening 644 which functions as a vent. Top portion 612 includes portion 645 that is located between opening 640 and vent 644. Cartridge 642 comprises frame member 646 and fragrance member 648 that is attached to frame member 646. Fragrance member 648 provides a fragrance or aroma when heat is applied thereto. Fragrance member 648 can be fabricated from the same material used to fabricate fragrance member 550 (see FIG. 21) which is described in the foregoing description. Opening 640 allows cartridge 642 to be removably positioned within bottom section 604. When cartridge 642 is positioned within bottom section 604, frame member 646 is visible and accessible through opening 640, and fragrance member 648 is visible through opening 644. Heating element 630 is located at a predetermined position within bottom section 604 so that when cartridge 642 is positioned within bottom section 604, fragrance member 648 is positioned adjacent to heating element 630 (see FIGS. 34 and 40).

In order to use apparatus 600, the user first pivots top section 602 to the position shown in FIG. 35. The user then pivots USB connector 620 in the direction indicated by arrow 650 shown in FIG. 36. Next, the user then pivots top section 602 so that it is repositioned in its original position (see FIGS. 38 and 39). The user is ready to plug USB connector 620 into a USB port of a computer or peripheral device. When the user plugs USB connector 620 into a corresponding USB port of a device that is operating, electrical power is applied to printed circuit section 624. As a result, electrical power is applied to heating element 630. In response to the electrical power, heating element 630 generates heat which causes fragrance member 648 to emit a fragrance or aroma which passes through opening 644. As described in the foregoing description, the opening 644 functions as a vent.

Once the user removes USB connector 620 from the USB port of the computer or peripheral device, the electrical power previously applied to resistor 630 is discontinued. The user then pivots top section 602 to the position shown in FIGS. 35 and 36. Next, the user then pivots USB connector 620 in a direction that is opposite arrow 650 (see FIG. 36) so that USB connector 620 is positioned as shown in FIG. 35. The user then pivots top section 602 so that it is positioned as shown in FIGS. 31 and 32 so as to cover USB connector 620.

When fragrance member 648 no longer provides the desired level of fragrance or aroma, the user can replace cartridge 642 with a new cartridge having a fresh fragrance member.

Figure 41:
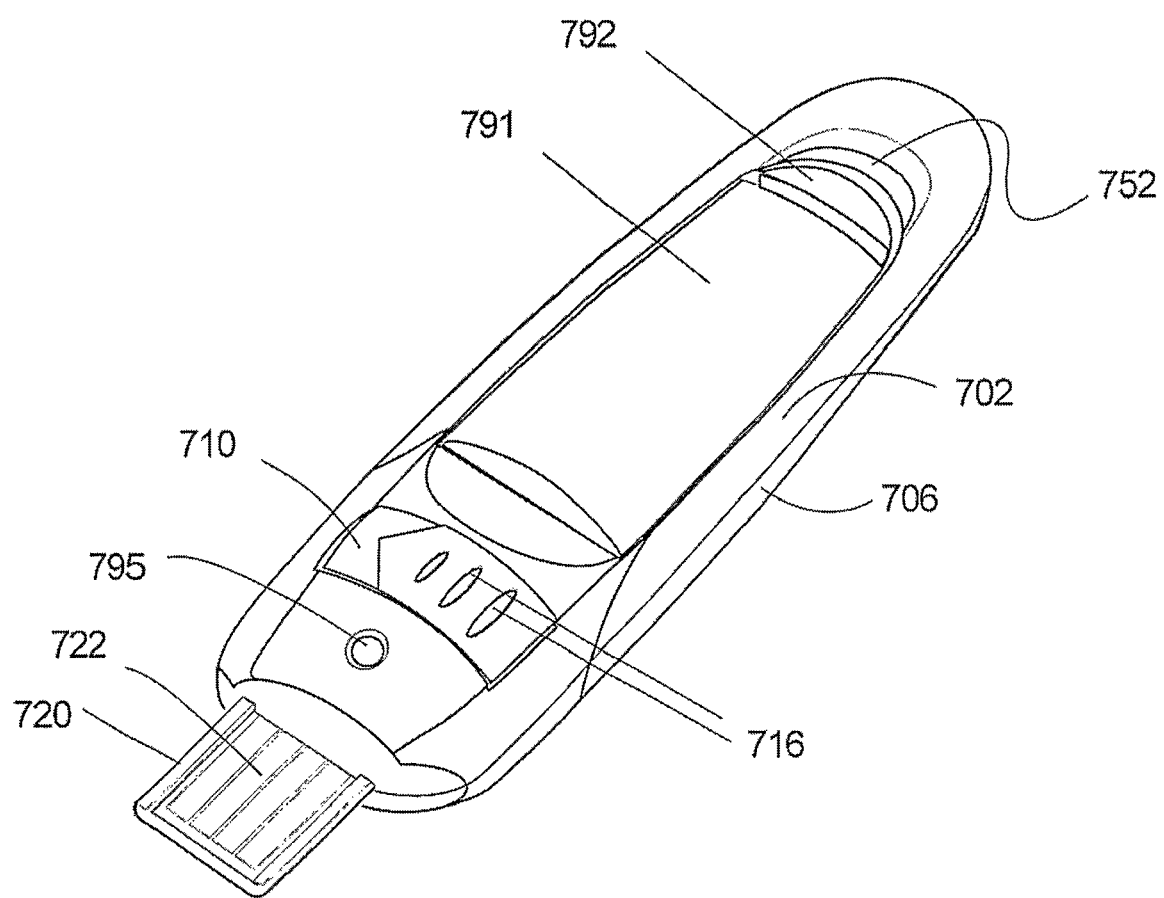
FIG. 41 is a perspective view of a fragrance emitting apparatus in accordance with another embodiment of the present invention.
Figure 44:
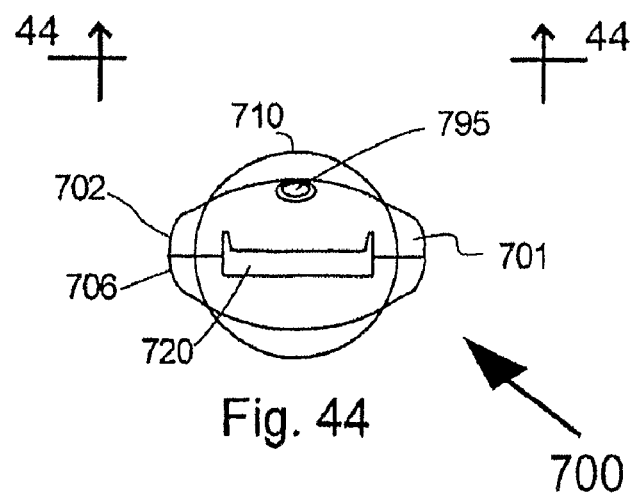
FIG. 44 is a view taken along line 44-44 of FIG. 42.
Figure 46:
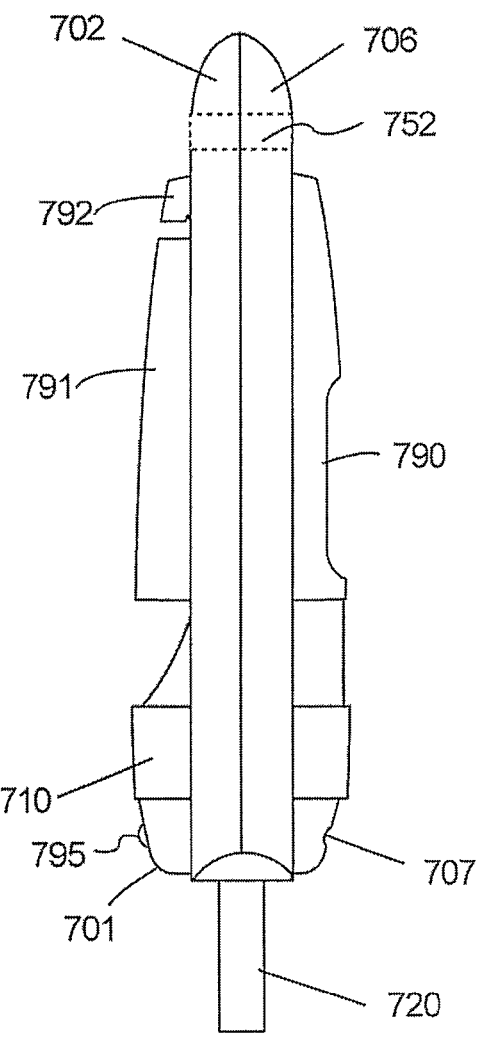
FIG. 46 is a side view, in elevation, taken along line 46-46 of FIG. 45.

Referring to FIGS. 41, 44 and 46, there is shown fragrance emitting apparatus 700 in accordance with a further embodiment of the present invention. Fragrance emitting apparatus 700 comprises casing 701 that has top section 702 and bottom section 706. Apparatus 700 further comprises a USB connector 720 which has printed circuit section 722. USB connector 720 functions in the same manner as USB connector 520 described in the foregoing description (see FIG. 27). Apparatus 700 includes a through-opening 752 through which a strap or chain can be inserted so as to allow the user to hang apparatus 700 around his or her neck or to hang the apparatus 700 on a hook, etc. Apparatus 700 includes LED (light-emitting diode) 795 that is electrically connected to printed circuit section 722. When USB connector 720 is connected to a USB port (not shown) of an operating computer or peripheral device, LED 795 illuminates. Apparatus 700 further comprises door 791 that is pivotally attached to top section 702 of casing 701. Door 791 includes spring-lock 792 which secures door 791 in a closed position. The purpose of door 791 will be explained in the ensuing description.

Figures 42, 43:
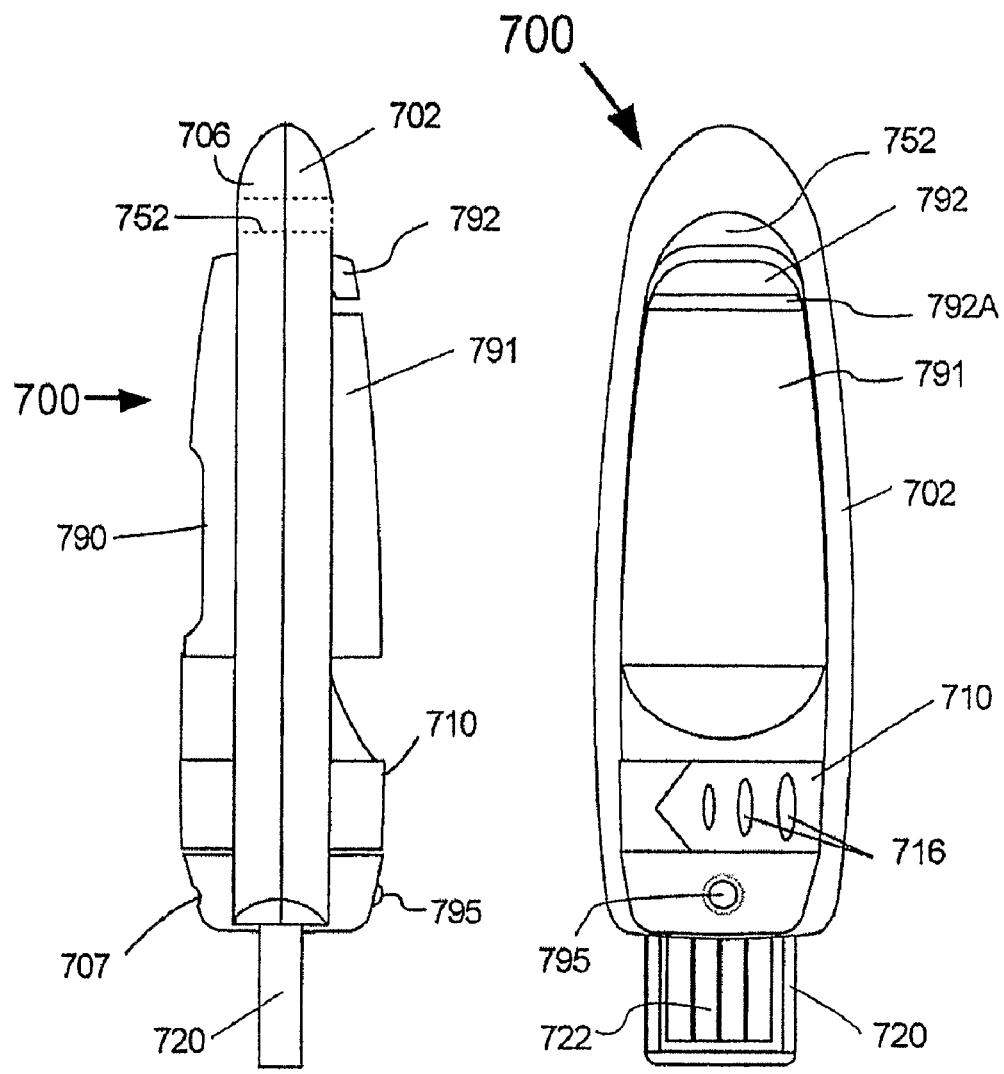
FIG. 42 is a top plan view of the fragrance emitting apparatus of FIG. 41.
FIG. 43 is a side view, in elevation, of the fragrance emitting apparatus of FIG. 41.

Apparatus 700 further comprises a vent system that comprises a rotatable member 710 and vent 718. Rotatable member 710 is positioned in casing 701 and is configured to rotate between two positions. A portion of rotatable member 710 is exposed at the top side of casing 701 (see FIG. 42) and a portion of rotatable member 710 is exposed at the bottom side of casing 701 (see FIG. 45). Rotatable member 710 has vent 716 and therefore, vent 716 rotates with member 710. Vent 718 is located in top section 702 of casing 701. Vent 718 is in communication with the interior 770 of casing 701. Rotatable member 710 is rotated between a first position wherein vent 716 is aligned with vent 718, and a second position wherein vent 716 is not aligned with vent 718 thereby closing off vent 718.

Figure 47:
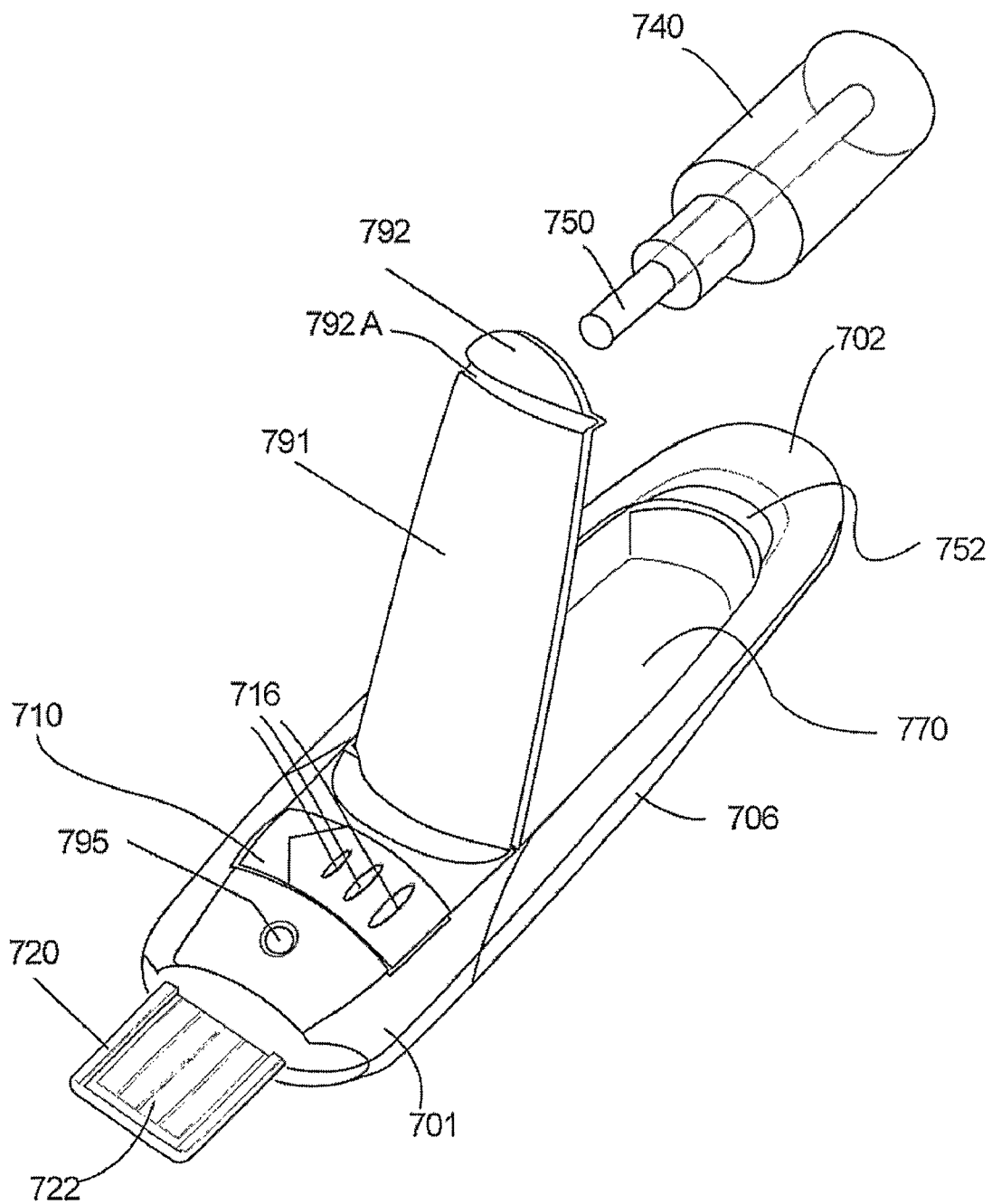
FIG. 47 is an exploded view, in perspective, of the fragrance emitting apparatus of FIG. 41.
Figure 48:
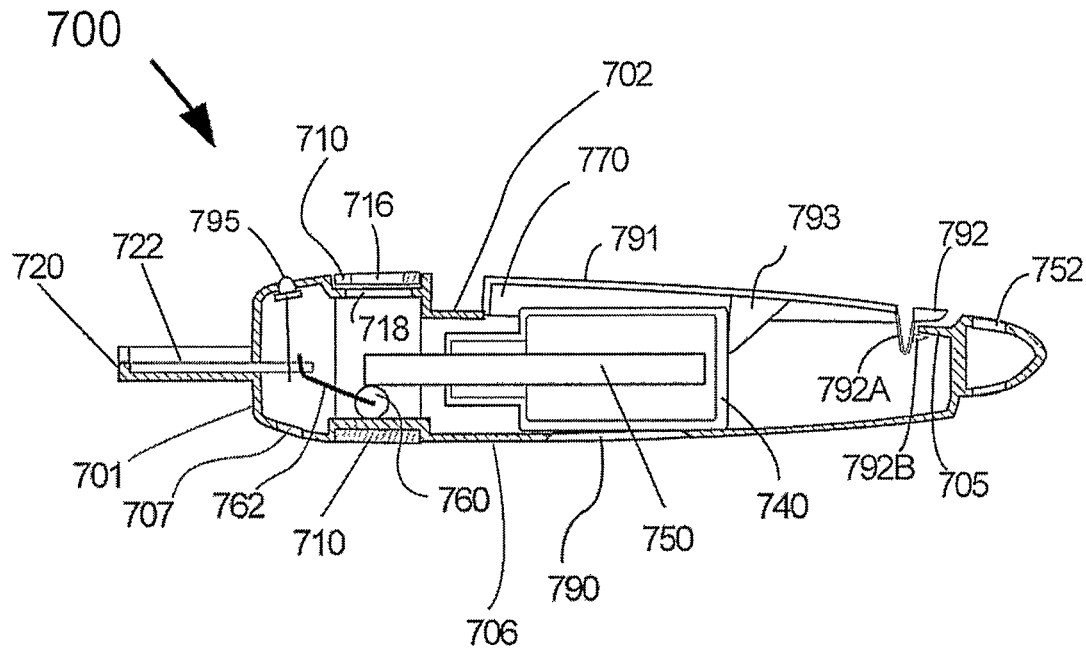
FIG. 48 is a cross-sectional view of the fragrance emitting apparatus of FIG. 41.
Figure 49:
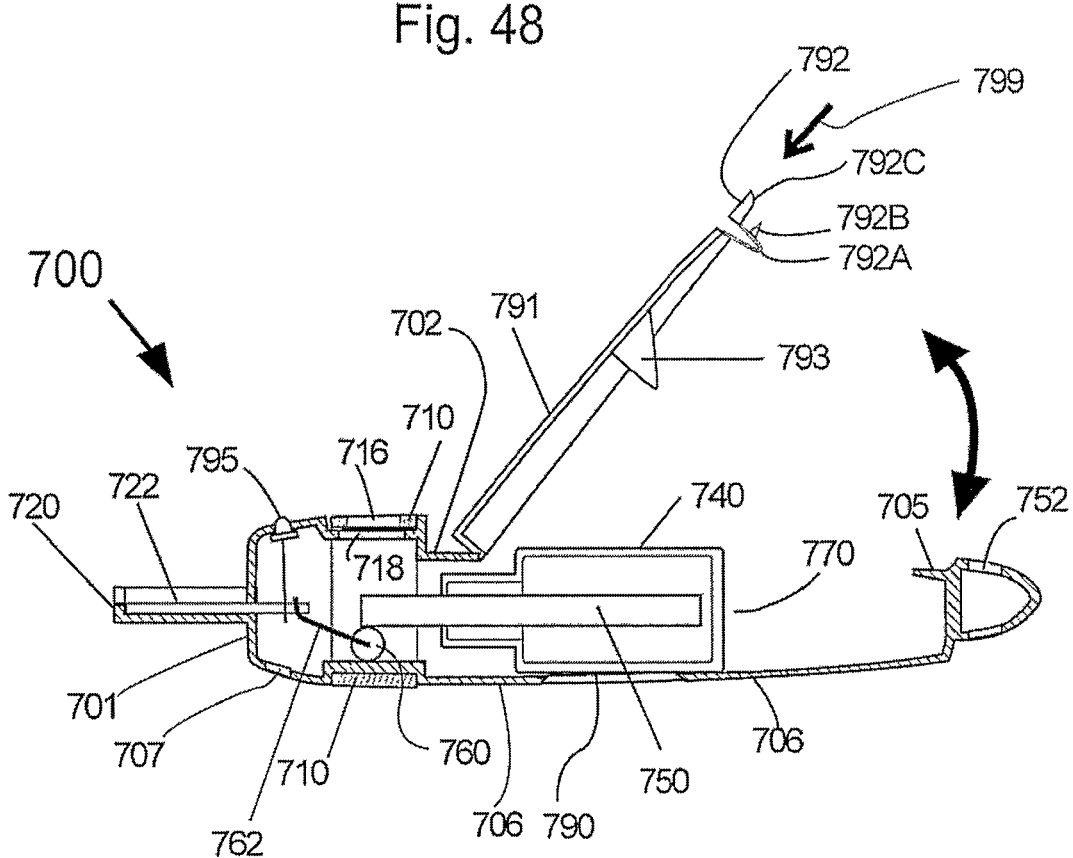
FIG. 49 is another cross-sectional view of the fragrance emitting apparatus of FIG. 41, the view showing a door of the fragrance emitting apparatus in an open position.

Referring to FIGS. 47-49, apparatus 700 has an interior 770 that is sized to receive fragrance bottle 740. Fragrance bottle 740 includes a fragrance member 750 that extends from fragrance bottle 740. Fragrance bottle 740 contains a liquid such as perfume or oil that has a desired fragrance. Fragrance member 750 is configured as an absorbent material that absorbs the liquid in fragrance bottle 740. As shown in FIGS. 48 and 49, apparatus 700 further comprises heating element 760. Heating element 760 can be configured as a device or electrical component that generates heat when electrical power is applied thereto. In one embodiment, heating element 760 is a resistor. Heating element 760 is electrically connected to printed circuit section 722 of USB connector 720 by electrically conductive lead or leads 762. The electrically conductive lead 762 has a degree of stiffness that allows heating element 760 to be positioned adjacent to fragrance member 750. When fragrance bottle 740 is positioned within interior 770 of apparatus 700 (see FIG. 48), fragrance member 750 contacts heating element 760. Once the fragrance bottle 740 is positioned within interior 770, the user may close door 791. Door 791 includes stopper member 793 that abuts fragrance bottle 740 when door 791 is closed (see FIG. 48) and thus, prevents movement of fragrance bottle 740.

Figure 45:
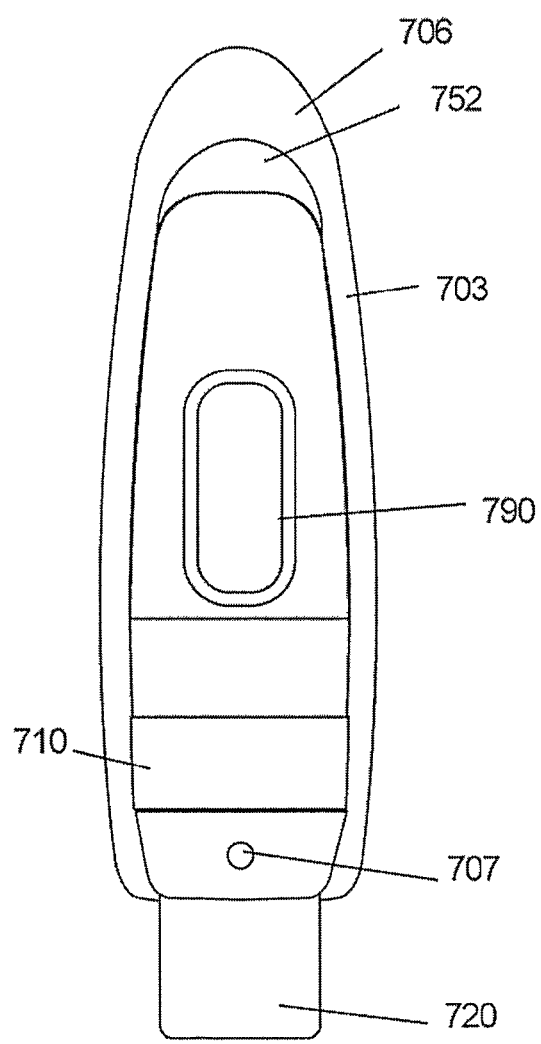
FIG. 45 is a bottom view of the fragrance emitting apparatus of FIG. 41.

Referring to FIGS. 48 and 49, spring lock 792 further comprises a resilient generally "V" shaped member 792A and a projection 792B is attached to the generally "V" shaped member 792A. In order to operate spring lock 792, the user pushes tip 792C in the direction indicated by arrow 799, and then lowers door 791 so that projection 792B is positioned underneath extending lip 705 of top section 702. Once projection 792B is underneath extending lip 705, the user then releases tip 792C so that "V" shaped member 792A expands to its normal position thereby maintaining projection 792B beneath extending lip 705 and causing projection 792B to abut extending lip 705. As a result, door 791 remains closed until the user decides to re-open door 791. In order to open door 791, the user pushes upon tip 792C so as to compress "V" shaped member 792A and cause projection 792B to move out from under extending lip 705. The user then lifts door 791 upward. As shown in FIGS. 45 and 46, apparatus 700 further includes an opening 790 which functions as a window. Opening 790 allows a user to view the interior 770 of casing 701 without opening door 791.

Referring to FIGS. 48 and 49, in order to use apparatus 700, a user rotates rotatable member 710 so that vent 716 is aligned with vent 718. Next, the user plugs USB connector 720 into a USB port (not shown) of an operating computer or peripheral device so that electrical power is applied to printed circuit section 722 and hence, heating element 760. As a result, heating element 760 generates heat that causes fragrance member 750 member to emit the fragrance or scent associated with the liquid in fragrance bottle 740. The fragrance or scent exits casing 701 through vents 716 and 718. When all the fragrance liquid in fragrance bottle 740 has been used, the user can open door 791 and replace fragrance bottle 740 with a new fragrance bottle.

Casing 701 and door 791 may be manufactured from any one of a variety of suitable materials, e.g. plastic.

All of the embodiments of the apparatus of the present invention described in the foregoing description may be fabricated from any suitable material, e.g. plastic, resin, composite, cardboard, wood, etc.

The foregoing description of the preferred embodiments of the invention has been presented for purposes of illustration and description only. It is neither intended to be exhaustive nor to limit the invention to the precise form disclosed; and obviously many modifications and variations are possible in light of the above teaching. Such modifications and variations that may be apparent to a person skilled in the art are intended to be included within the scope of this invention as defined by the accompanying claims.

What is claimed is:

1. A USB flash memory drive comprising:
    a housing having an interior and a vent in communication with the interior;
    an electronic support member within and connected to the housing;
    an electronic component mounted on the electronic support member, the electronic component generating heat when the USB flash memory drive is in use;
    a USB connector joined to the electronic support member and extending from the housing;
    a stationary device located within and connected to the housing, the stationary device containing a substance that emits a fragrance, scent or aroma when heat is applied to the stationary device; and
    wherein the stationary device is proximate to the electronic component so that heat generated by the electronic component causes the stationary device to emit the fragrance, scent or aroma wherein such fragrance, scent or aroma exits the interior of the housing through the vent.

2. A fragrance emitting apparatus for connection to a USB port, comprising:
    a casing having an interior and a fragrance vent in communication with the interior;
    a heating element located within the casing that generates heat when electrical power is applied thereto;
    a USB connector connected to the casing and electrically connected to the heating element so as to provide electrical power to the heating element when the USB connector is connected to a USB port; a stationary fragrance member located within the casing to provide a fragrance, scent or aroma when heat is applied to the stationary fragrance member, the stationary fragrance member being proximate to the heating element so that heat generated by the heating element causes the stationary fragrance member to emit a fragrance, scent or aroma which exits the interior of the casing through the vent.

3. The fragrance emitting apparatus according to claim 2 wherein the casing has a top portion and a bottom portion, the fragrance vent being in the top portion and aligned with the stationary fragrance member.

4. The fragrance emitting apparatus according to claim 3 wherein the top portion has a generally concave-shaped cover portion that is positioned adjacent to the stationary fragrance member, the fragrance vent being generally centrally located in the concave-shaped cover portion, the concave-shaped cover portion facilitating insertion into the fragrance vent a fragrance-emitting substance that replenishes the stationary fragrance member.

5. The fragrance emitting apparatus according to claim 3 wherein the bottom portion of the casing has an air vent that allows air to flow into the interior of the casing.

6. The fragrance emitting apparatus according to claim 2 wherein the fragrance emitting apparatus has a shape that is substantially the same as the shape of a USB flash memory drive.

7. The fragrance emitting apparatus according to claim 2 further comprising a protective tab comprising a first portion exterior to the casing and a second portion located within the casing and positioned between the stationary fragrance member and the fragrance vent, the protective member being removable such that a user may pull the first portion and remove the second portion from between the stationary fragrance member and the fragrance vent.

8. A fragrance emitting apparatus for connection to a USB port, comprising:
    a casing having a first end, an opposite second end, an interior and a slot in the second end which is in communication with the interior, the casing including a vent in communication with the interior;
    a cartridge having a first portion removably positioned within the interior of the casing and a second portion extending from the slot, the cartridge comprising a fragrance member attached to the first portion, the fragrance member providing a fragrance, scent or aroma when heat is applied thereto;
    a USB connector connected to the second end of the casing, the USB connector having an electrically conductive printed circuit section;
    a heating element positioned within the interior of the casing and electrically connected to the electrically conductive printed circuit section, the heating element being positioned adjacent to the fragrance member, the heating element generating heat when electrical power is applied thereto;
    wherein heat generated by the heating element causes the fragrance member to emit a fragrance, scent or aroma which exits the interior of the casing through the vent in the casing; and
    a vent cover slidably attached to the casing and having an opening therein, the vent cover being slidable between a closed position wherein the vent cover covers the USB connector and the opening in the vent cover is not aligned with the vent in the casing, and an open position wherein the USB connector is exposed and the opening in the vent cover is aligned with the vent in the casing.

9. The fragrance emitting apparatus according to claim 8 wherein the casing comprises a top section and a bottom section, the vent cover being slidably attached to the top section.

10. The fragrance emitting apparatus according to claim 8 wherein the slot in the casing is sized to create a slight frictional relationship between the second portion of the cartridge and the portion of the casing that extends about the slot so as to prevent the cartridge from falling out of the slot.

11. The fragrance emitting apparatus according to claim 9 wherein the vent in the casing is located in the top section of the casing.

12. The fragrance emitting apparatus according to claim 9 wherein the bottom section of the casing includes an air vent to allow airflow through the interior of the casing.

13. The fragrance emitting apparatus according to claim 8 wherein the vent cover has a portion covered with small protrusions to provide friction for a user's finger when sliding the cover between the closed and open position.

14. The fragrance emitting apparatus according to claim 8 wherein the second portion of the cartridge comprises means to secure a chain or strap to the second portion.

15. The fragrance emitting apparatus according to claim 8 wherein the fragrance emitting apparatus has the shape of a flash drive.

16. A fragrance emitting apparatus for connection to a USB port, comprising:
    a casing having a top casing section and a bottom casing section, the top casing section having a vent, the bottom casing section having an interior, a top portion having a recessed area, a main opening in communication with the interior and a vent in communication with the interior, the top casing section being rotatably attached to the bottom casing section and rotatable to an open position wherein the top portion of the bottom casing section is totally exposed and to a closed position wherein the top casing section covers the entire top portion of the bottom casing section and the vent of the top casing section is aligned with the vent of the bottom casing section;
    a USB connector pivotally attached to the bottom casing section and pivotal within the recessed area to a first position wherein the USB connector extends from the casing, and a second position wherein the USB connector is located entirely within the recessed area and covers the vent in the top portion of the bottom casing section, the USB connector being pivotal about an electrically conductive pivot pin and having a circuit section that is electrically connected to the electrically conductive pivot pin;
    wherein when the USB connector is in the second position and the top casing section is in the closed position, the top casing section covers the USB connector;
    a cartridge removably positioned within the interior of the bottom casing section, the cartridge comprising a frame member and a fragrance member attached to the frame member, the frame member being accessible through the main opening and the fragrance member being visible through the vent of the bottom casing section, the fragrance member providing a fragrance, scent or aroma when heat is applied thereto;
    a heating element positioned within the interior of the bottom casing section and electrically connected to the electrically conductive pivot pin, the heating element being positioned adjacent to the fragrance member, the heating element generating heat when electrical power is applied thereto; and wherein heat generated by the heating element causes the fragrance member to emit a fragrance, scent or aroma which exits the interior of the casing through the vent in the top portion of the bottom casing section.

17. The fragrance emitting apparatus according to claim 16 further comprising an electrically conductive member connected between the heating element and the electrically conductive pivot pin.

18. The fragrance emitting apparatus according to claim 16 wherein the vent in the top casing section comprises a plurality of differently shaped through-holes.

19. The fragrance emitting apparatus according to claim 18 wherein the bottom casing section has a bottom portion and wherein the fragrance emitting apparatus further includes a second air vent in the bottom portion of the bottom casing section, the second air vent being in communication with the interior of the bottom casing section.

20. The fragrance emitting apparatus according to claim 16 wherein the fragrance emitting apparatus has an overall shape that resembles a piece of jewelry.

\* \* \* \* \*